(12) United States Patent
Stacey et al.

(10) Patent No.: US 9,624,500 B2
(45) Date of Patent: Apr. 18, 2017

(54) METABOLIC ENGINEERING OF PLANTS FOR INCREASED HOMOGENTISATE AND TOCOCHROMANOL PRODUCTION

(71) Applicants: Gary Stacey, Columbia, MO (US); Minviluz G. Stacey, Columbia, MO (US)

(72) Inventors: Gary Stacey, Columbia, MO (US); Minviluz G. Stacey, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 694 days.

(21) Appl. No.: 13/958,397

(22) Filed: Aug. 2, 2013

(65) Prior Publication Data

US 2014/0041076 A1    Feb. 6, 2014

Related U.S. Application Data

(60) Provisional application No. 61/679,029, filed on Aug. 2, 2012.

(51) Int. Cl.
| | | |
|---|---|---|
| *A01H 5/10* | (2006.01) | |
| *C12N 15/82* | (2006.01) | |
| *C12N 15/05* | (2006.01) | |
| *C12N 9/02* | (2006.01) | |

(52) U.S. Cl.
CPC ......... *C12N 15/8247* (2013.01); *A01H 5/10* (2013.01); *C12N 9/0069* (2013.01); *C12N 15/8216* (2013.01); *C12N 15/8218* (2013.01); *C12N 15/8243* (2013.01); *C12N 15/8274* (2013.01); *C12Y 113/11005* (2013.01)

(58) Field of Classification Search
CPC ... C12N 15/8247; C12N 15/8216; A01H 5/10
See application file for complete search history.

(56) References Cited

U.S. PATENT DOCUMENTS

| | | | |
|---|---|---|---|
| 7,297,541 B2 | 11/2007 | Moshiri et al. | |
| 2001/0005749 A1* | 6/2001 | Cahoon | C12N 9/0069 536/23.2 |
| 2003/0182679 A1* | 9/2003 | Geiger | A23K 1/14 800/278 |
| 2004/0045051 A1* | 3/2004 | Norris | C12N 15/8243 800/278 |
| 2005/0289664 A1 | 12/2005 | Moshiri et al. | |

OTHER PUBLICATIONS

Full text of "9 steps in grading soybeans", U.S. Dept. of Agriculture, 1943.*

(Continued)

*Primary Examiner* — Russell Kallis
*Assistant Examiner* — Fan Weihua
(74) *Attorney, Agent, or Firm* — Dentons US LLP

(57) ABSTRACT

The invention provides methods and compositions for modifying tocochromanol biosynthesis in plants. The present invention thus surprisingly and beneficially provides for increasing desired tocochromanol compounds in plants and enhancing the nutritional quality of human food and animal feed, without associate deleterious plant phenotypes.

12 Claims, 6 Drawing Sheets

(56) References Cited

OTHER PUBLICATIONS

Fernández-Cañón, José M., and Miguel A. Peñalva. "Molecular characterization of a gene encoding a homogentisate dioxygenase from Aspergillus nidulans and identification of its human and plant homologues." Journal of Biological Chemistry 270.36 (1995): 21199-21205.*
Alonso, Jose M., et al. "Genome-wide insertional mutagenesis of Arabidopsis thaliana." Science 301.5633 (2003): 653-657.*
Han, Chengyun, et al. "Disruption of fumarylacetoacetate hydrolase causes spontaneous cell death under short-day conditions in Arabidopsis." Plant physiology 162.4 (2013): 1956-1964.*
SALK_027807, retrieved from www.arabidopsis.org.*
Soy products, Iowa State University Soybean Extension and Research Program, Mar. 21, 2007.*
Hammond, John P., et al. "Changes in gene expression in Arabidopsis shoots during phosphate starvation and the potential for developing smart plants." Plant Physiology 132.2 (2003): 578-596.*
Dixon, David P., and Robert Edwards. "Enzymes of tyrosine catabolism in Arabidopsis thaliana." Plant science 171.3 (2006): 360-366.*
GenBank Accession No. AF149017, Jun. 1, 2000.
GenBank Accession No. AAF73132.1, Jun. 1, 2000.
Karunanandaa at al., "Metabolically engineered oilseed crops with enhanced seed tocopherol," *Metabolic Engineering* 7(5-6):384-400, 2005.
Stacey, "Identification of a Soybean Fast Neutron Mutant with Increased Homogentisic Acid and Tocochromanol Accumulation," presentation at the *14th Biennial Molecular and cellular Biology of the Soybean Conference*, Aug. 2012.
Stacey et al., "Development of Transposon and Fast Neutron Mutants of Soybean for Functional Genomic Studies," *Plant Talks Seminar Series, University of Missouri, Columbia*, Feb. 2011.

* cited by examiner

METABOLIC ENGINEERING OF PLANTS FOR INCREASED HOMOGENTISATE AND TOCOCHROMANOL PRODUCTION

CROSS-REFERENCE TO RELATED APPLICATIONS

This applications claims the benefit of priority of U.S. Provisional Application Ser. No. 61/679,029, filed on Aug. 2, 2012, the disclosure of which is incorporated herein by reference in its entirety.

STATEMENT REGARDING FEDERALLY SPONSORED RESEARCH OR DEVELOPMENT

"This invention was made with government support under grant number 4688258 awarded by the National Science Foundation. The government has certain rights in the invention."

INCORPORATION OF SEQUENCE LISTING

The sequence listing that is contained in the file named "UVMO105US_ST25.txt", which is 89 kilobytes as measured in Microsoft Windows operating system and was created on Aug. 2, 2013, is filed electronically herewith and incorporated herein by reference.

BACKGROUND OF THE INVENTION

Field of the Invention

The present invention relates generally to the field of plant genetics and biochemistry. More particularly, it concerns methods and compositions for modifying homogentisic acid (HGA) and tocochromanol content in plants.

Description of Related Art

Tocochromanols such as Vitamin E are a group of plant-derived, lipid-soluble compounds with strong antioxidant activities. Since humans and animals cannot produce vitamin E, it has to be supplied in the daily diet. In addition to vitamer activity in fertility cases, there is a growing body of literature indicating that the strong anti-oxidative activity of tocochromanols is effective in counteracting the onset or progression of human diseases such as cancer and cardiovascular diseases. For these reasons, biofortification of plants for increased vitamin E content has been conducted in both academic and industrial laboratories.

SUMMARY OF THE INVENTION

In one aspect, the invention provides a plant in which a gene encoding homogentisic acid (HGA) dioxygenase (HGO) is down-regulated to confer increased HGA content, or a metabolic product derived therefrom, wherein the plant lacks deleterious morphological traits relative to a wild-type plant. In one embodiment, the plant is a soybean plant and the gene is the Glyma12g20220 gene. In other embodiments, such a plant comprises a non-transgenic mutation in the Glyma12g20220 gene resulting in the down-regulation. In still other embodiments of the invention, the mutation comprises a deletion, point mutation, or an insertion. In one embodiment of the invention, the mutation is produced by irradiation, T-DNA insertion, transposon insertion, or chemical mutagenesis.

In another aspect, a Glyma12g20220 or other HGO gene is down-regulated by expression of an antisense or RNA interference (RNAi) construct comprising a sequence complementary to all or a portion of an HGO gene messenger RNA (mRNA). In one embodiment of the invention, expression of such a construct is developmentally-regulated, organelle-specific, inducible, tissue-specific, constitutive, cell-specific, seed-specific, or germination-specific. In this manner, HGA and tocochromanol production may be engineered to specific portions of a plant, or at different developmental time. By manipulating specific steps in the metabolism of HGA and metabolites derived therefrom, different tocochromanols can be produced in different tissue types or different times.

In another aspect, plants in which an HGO gene such as Glyma12g20220 gene is down-regulated further comprises at least a first transgene that encodes an enzyme catalyzing at least one step in tocochromanol biosynthesis. In certain embodiments of the invention, the enzyme is selected from the group consisting of: MT1, tMT2, GMT, tyrA, HPT, tocopherol cyclase, chlorophyllase, dxs, dxr, GGPPS, AANT1, LTT1, IDI, GGH, HGGT, and HST.

In another aspect, the invention further relates to a plant part of a plant in which HGO is down-regulated. In one embodiment of the invention, the part of the plant is further defined as a protoplast, cell, meristem, root, pistil, anther, flower, seed, embryo, stalk or petiole. In another aspect, the invention further relates to a seed that produces a plant in which Glyma12g20220 or another HGO gene is down-regulated in accordance with the invention.

In yet another aspect, the invention provides a method of increasing production of HGA or a metabolic product derived therefrom in a plant comprising down-regulating HGO relative to an otherwise isogenic wild-type plant, wherein the plant in which down-regulating occurs lacks deleterious morphological traits relative to a wild-type plant. Non-limiting examples of such deleterious traits may include one or more of reduced germination, reduced vigor, reduced yield, and reduced hardiness to biotic or abiotic stress relative to an otherwise isogenic plant lacking the down-regulation. In one embodiment of such a method, the down-regulating comprises mutating a Glyma12g20220 gene or other HGO gene. In one embodiment of the invention, mutating comprises introducing a deletion, a point mutation, or an insertion in a wild-type Glyma12g20220 gene.

In another aspect of the invention, down-regulating HGO comprises introgressing into a plant or any given variety a mutated HGO allele. In a specific embodiment, the mutated allele comprises the mutated Glyma12g20220 allele contained in a representative sample of seed of the plant designated MO12 deposited with the ATCC under Accession No. PTA-12919. In another embodiment of the invention, down-regulating comprises expressing in the plant an antisense or RNAi construct comprising a sequence complementary to all or a portion of a HGO messenger RNA (mRNA). In one embodiment of the invention, expressing is developmentally-regulated, organelle-specific, inducible, tissue-specific, constitutive, cell-specific, seed-specific, or germination-specific.

In another aspect, the invention further relates to expressing in the plant in which the HGO gene is down-regulated a transgene that encodes an enzyme catalyzing at least one step in tocopherol biosynthesis.

In yet another aspect, the invention provides a method for producing a commercial product comprising obtaining a plant of the invention in which HGO is down-regulated, or a part thereof, and producing a commercial product therefrom. In one embodiment of the invention, commercial products include protein concentrate, protein isolate, grain, hulls, meal, flour or soil.

In further aspects, the plant comprises an antisense or RNAi construct comprising a DNA molecule complementary to all or a portion of a HGO mRNA, wherein the DNA molecule down-regulates the function of the gene relative to a plant lacking the DNA molecule. In one embodiment of the invention, a DNA molecule is operably linked to a developmentally-regulated, organelle-specific, inducible, tissue-specific, constitutive, cell-specific, seed specific, or germination-specific promoter.

In yet another aspect, the present invention provides a method of conferring at least a first altered agronomic property to a plant comprising down-regulating an HGO gene function in the plant relative to a plant in which HGO gene function is not down-regulated. In one embodiment of the invention, altered agronomic properties can include increased HGA, increased vitamin E, increased isoforms of vitamin E, increased precursors of vitamin E, increased tocochromanols, increased tocopherols, increased γ-tocopherols, increased β-tocopherols, and increased tocotrienols.

Embodiments discussed in the context of methods or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

BRIEF DESCRIPTION OF THE SEQUENCES

Homogentisic acid dioxygenase (HGO) cDNA and protein sequences from selected plants.
SEQ ID NO: 1—cDNA sequence of Glyma12g20220 *Glycine max* (soybean)
SEQ ID NO: 2—protein sequence
SEQ ID NO: 3—cDNA sequence of Glyma06g34940.1
SEQ ID NO: 4—protein sequence
SEQ ID NO: 5—cDNA sequence of Glyma06g34890.1
SEQ ID NO: 6—protein sequence
SEQ ID NO: 7—cDNA sequence of LOC_Os06g01360 *Oryza sativa* (rice; Japonica Group)
SEQ ID NO: 8—protein sequence
SEQ ID NO: 9—protein sequence LOCUS ID: OsI_21275 *Oryza sativa* (rice; Indica Group)
SEQ ID NO: 10—cDNA sequence of GRMZM2G154093 *Zea mays* (corn)
SEQ ID NO: 11—protein sequence
SEQ ID NO: 12—cDNA sequence of Phvulv091012528m *Phaseolus vulgaris* (common bean)
SEQ ID NO: 13—protein sequence
SEQ ID NO: 14—cDNA sequence of 30209.m001534 *Ricinus communis* (castor oil)
SEQ ID NO: 15—protein sequence
SEQ ID NO: 16—cDNA sequence of Lus 10042839 Common flax or linseed
SEQ ID NO: 17—protein sequence
SEQ ID NO: 18—cDNA sequence of POPTR_0001s38310.1 *Populus trichocarpa* (Western Balsam poplar or California poplar)
SEQ ID NO: 19—protein sequence
SEQ ID NO: 20—cDNA sequence of Sb10g000360.1 *Sorghum bicolor* (sorghum)
SEQ ID NO: 21—protein sequence
SEQ ID NO: 22—cDNA sequence of Pavirv00023476m *Panicum virgatum* (switchgrass)
SEQ ID NO: 23—protein sequence
SEQ ID NO: 24—cDNA sequence of cassava4.1_012571m *Manihot esculenta* (cassava)
SEQ ID NO: 25—protein sequence SEQ ID NO: 26—cDNA sequence of homogentisate 1,2-dioxygenase (HGO; GenBank Accession No. AF149017) *Lycopersicon esculentum*
SEQ ID NO: 27—protein sequence GenBank Accession No. AAF73132.1
SEQ ID NO: 28—cDNA sequence of AT5G54080 *Arabidopsis thaliana*
SEQ ID NO: 29—protein sequence

DETAILED DESCRIPTION OF THE INVENTION

Figure 4:
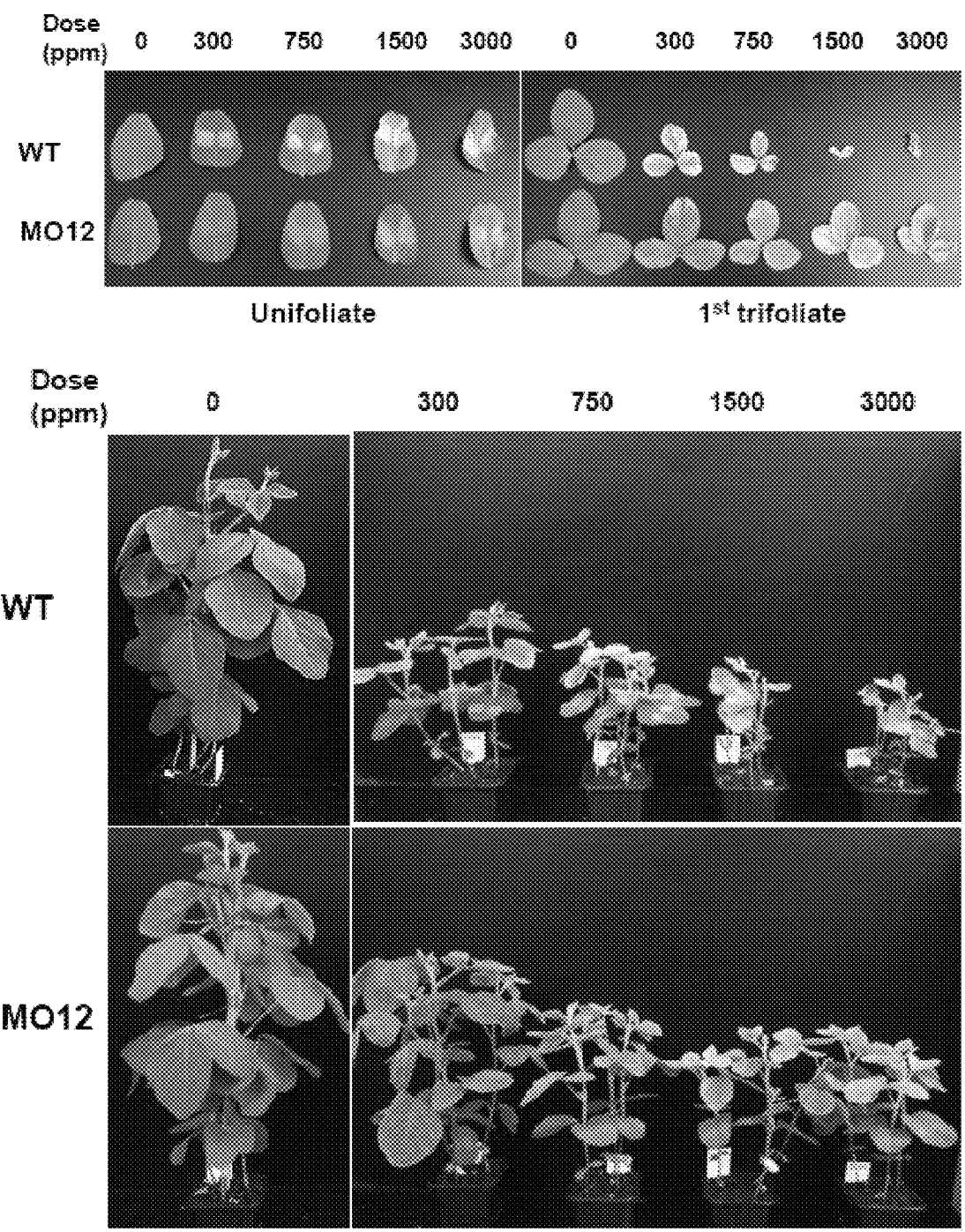
FIG. 4 shows increased resistance of MO12 plants to the commercial herbicide CALLISTO® (Syngenta Crop Protection, USA), which inhibits 4-hydroxyphenylpyruvate dioxygenase (4-HPPD), as compared to Williams 82 (WT).
Figure 5:
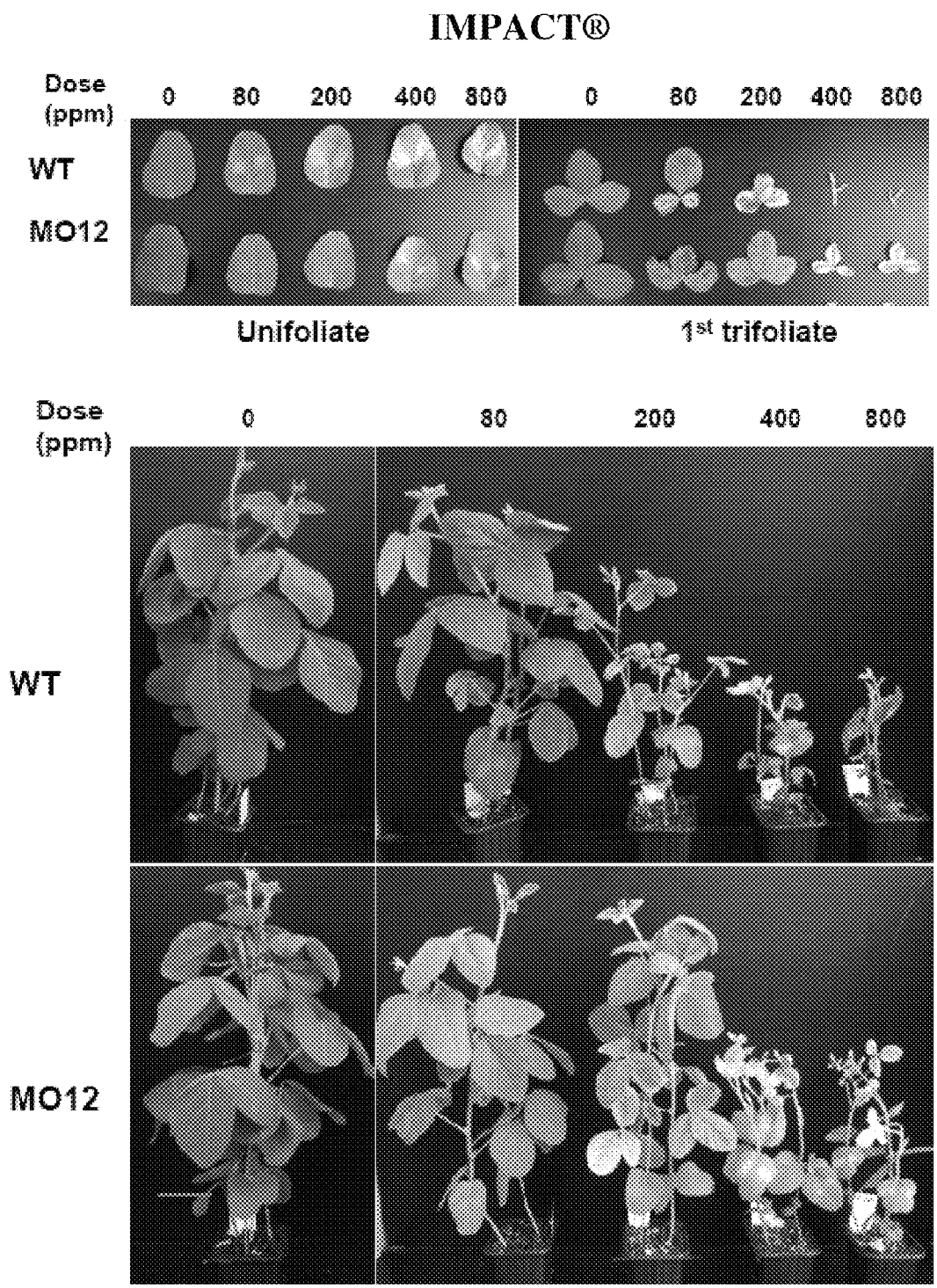
FIG. 5 shows increased resistance of MO12 plants to the commercial herbicide IMPACT® (IMVAC, USA), which inhibits 4-hydroxyphenylpyruvate dioxygenase (4-HPPD), as compared to Williams 82 (WT).
Figure 6:
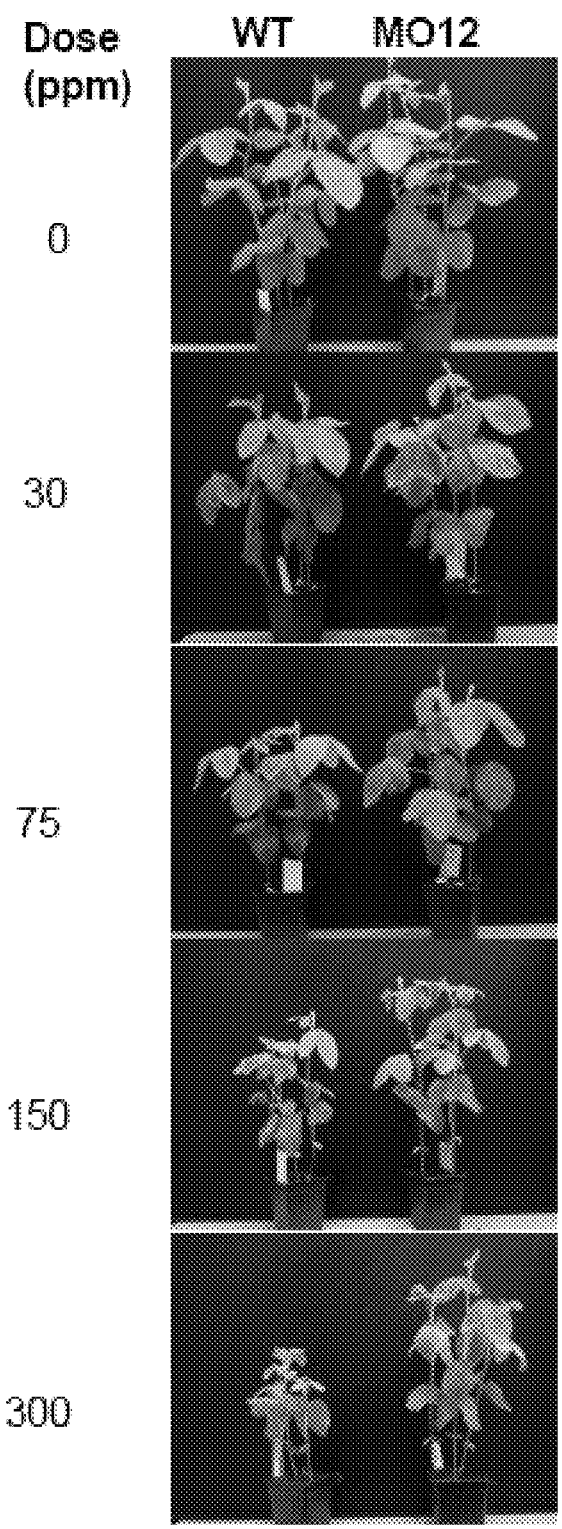
FIG. 6 shows increased resistance of MO12 plants to the commercial herbicide LAUDIS® (Bayer CropScience, USA), which inhibits 4-hydroxyphenylpyruvate dioxygenase (4-HPPD), as compared to Williams 82 (WT).

The present invention provides methods and compositions for increased homogentisic acid (HGA) and tocochromanol metabolites thereof in plants without deleterious morphological traits associated with prior attempts to engineer tocochromanols in plants. In certain aspects this comprises down-regulating the expression of HGA dioxygenase (HGO) encoded by the Glyma12g20220 gene. The present invention thus surprisingly and beneficially provides for: 1) increasing tocopherol and tocotrienol concentration in plants; 2) enhancing the nutritional quality of human food and animal feed; 3) increasing the ability of plants to cope with abiotic and biotic stresses. In certain aspects the invention may also be used to provide increased tolerance of plants to certain classes of herbicides, such as HPPD inhibitor herbicides (FIGS. 4, 5, and 6).

Figure 1:
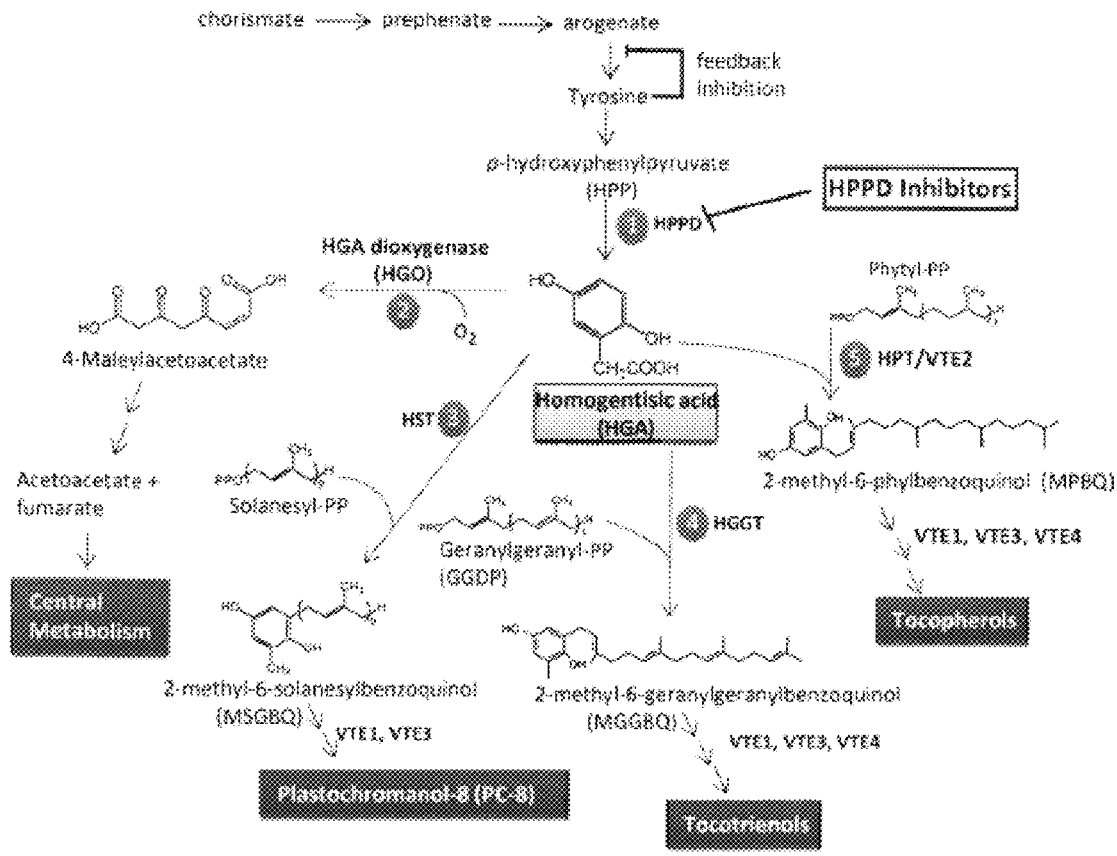
FIG. 1 shows the tocochromanol biosynthetic pathway in plants. The immediate steps in HGA formation and its utilization for central metabolism or tocochromanol production are numbered. HPPD=p-hydroxyphenylpyruvate dioxygenase; HGGT=HGA geranylgeranyl transferase; HPT=HGA phytyl transferase; HST=HGA solanesyl transferase; VTE1=tocopherol cyclase; VTE3=MPBQ/MSBQ methyl transferase; VTE4=γ-tocopherol methyl transferase.

The tocochromanol biosynthetic pathway in higher plants, which includes tocopherol, tocotrienols and plastochromanol-8, involves a number of enzymes (Table 1). HGO, however, catalyzes the conversion of HGA to 4-maleylacetoacetate and thus reduces the pool of available HGA for tocochromanol biosynthesis. HGA is a common precursor to both tocopherols and plastoquinones. The plastids of higher plants exhibit interconnected biochemical pathways leading to secondary metabolites including tocopherols (FIG. 1). The various genes and their encoded proteins involved in tocopherol biosynthesis are listed in Table 1.

TABLE 1

Tocochromanol biosynthesis coding regions and enzymes.

| Coding region or Enzyme Abbreviation | Enzyme name |
| --- | --- |
| tyrA | Mono or bifunctional prephenate dehydrogenase |
| HPT | Homogentisate prenyl transferase |
| DXS | 1-Deoxyxylulose-5-phosphate synthase |
| DXR | 1-Deoxyxylulose-5-phosphate reductoisomerase |
| GGPPS | Geranylgeranyl pyrophosphate synthase |
| HPPD | p-Hydroxyphenylpyruvate dioxygenase |
| AANT1 | Adenylate transporter |
| IDI | Isopentenyl diphosphate isomerase |
| MT1 | Bacterial 2-methylphytylplastoquinol |
| tMT2 | Plant 2-methylphytylplastoquinol methyltransferase |
| GGH | Geranylgeranyl diphosphate reductase |
| Slr1737 | Tocopherol cyclase |
| GMT | Tocopherol gamma methyl transferase |
| LTT1 | Phytol kinase |
| Chl1 and Chl2 | Chlorophyllase 1 and 2 |
| HGGT | HGA geranylgeranyl transferase |
| HST | HGA solanesyl transferase |

The synthesis of all tocochromanols is initiated by the conversion of 4-hydroxyphenylpyruvate (HPP) into homogentisic acid (HGA) catalyzed by HPP dioxygenase (HPPD). The Shikimate pathway that synthesizes HPP from chorismate is under feedback inhibition, limiting the flux of HPP and hence also limiting HGA formation. HGA can be prenylated for the formation of the various vitamin E isoforms (i.e. tocopherols, tocotrienols and plastochromanol-8) or it can be oxidized to 4-maleylacetoacetate which is eventually funneled to central metabolism as acetoacetate and fumarate (FIG. 1). The present inventors show that a large portion of synthesized HGA is converted to 4-maleylacetoacetate and that manipulations to prevent the formation of functional HGA dioxygenase (HGO) result in significantly increased HGA flux in plants.

The present invention thus provides methods that increases HGA flux by blocking the pathway towards 4-maleylacetoacetate formation from HGA, and can be applied to other agronomically important crops besides soybean. Moreover, this invention covers any genetic manipulations to disrupt the formation of functional HGO enzymes in plants.

Figure 2:
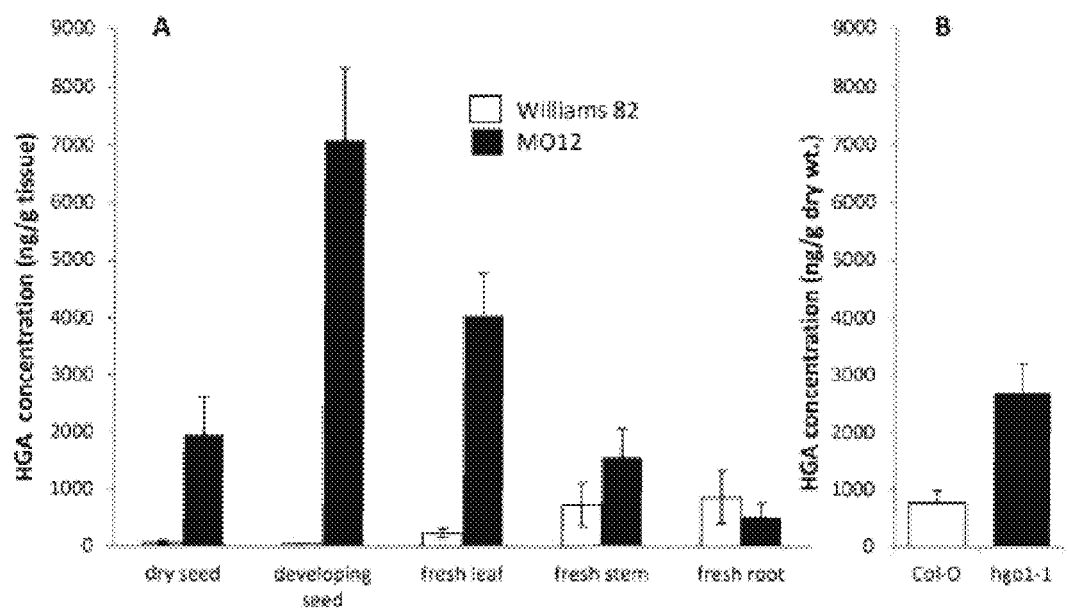
FIG. 2 shows mutations in HGA dioxygenase (HGO) result in increased HGA accumulation in various (A) soybean tissues and in (B) Arabidopsis seeds. Soybean cultivar MO12 carries a deletion in Glyma12g20220 whereas Arabidopsis line hgo1-1 carries a T-DNA insertion in At5g54080. Williams 82 and Col-0 are the unmodified parental lines for the soybean and Arabidopsis mutants, respectively. HGA concentrations were determined by LC-MS. Standard deviation for each data is shown.

Efforts aimed at the biofortification of plants for increased vitamin E content have elucidated that one major factor limiting increased vitamin E production by plants is the accumulation of the metabolite HGA. The present invention represents a novel approach of increasing HGA accumulation in plants. HGA content is increased in various tissues and in seeds of soybean. For example, in soybean, deletion of gene Glyma12g20220 (encoding HGO) in cultivar MO12 (derived from cv. Williams 82) resulted in a 31- and 124-fold increase in HGA accumulation in mature and green seeds (stage R6), respectively (FIG. 2A). Vegetative tissues, such as leaves and stems, also accumulated 17- and 2-fold higher HGA, respectively.

Figure 3:
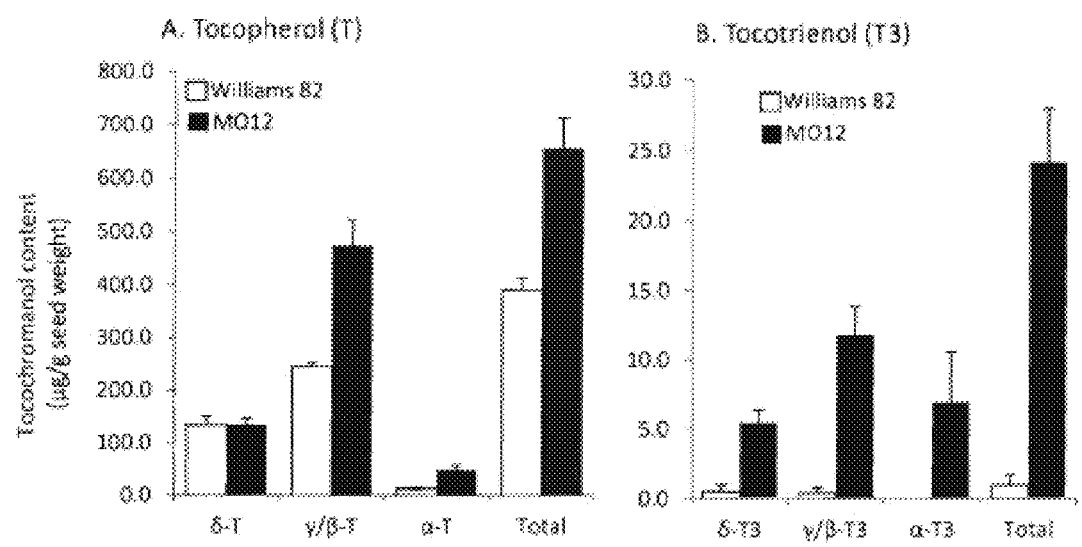
FIG. 3 shows tocochromanol content in Williams 82 (wild type) and MO12 seeds.

Deletion of Glyma12g20220 was induced by fast neutron irradiation and was detected by comparative genome hybridization (CGH). Consistent with this result, disruption of the *Arabidopsis* HGO gene (At5g54080) by T-DNA insertion resulted in a 3.5-fold increase in HGA accumulation in seeds (FIG. 2B). In soybean, increased HGA flux in cultivar MO12 also resulted in increased accumulation of tocochromanols (FIG. 3). Total tocochromanol (tocopherol+tocotrienol) content in mature seeds increased by ~2-fold, mostly as γ- and β-tocopherols. Soybean seeds normally do not produce detectable amounts of tocotrienols. Cultivar MO12, however, produces 27-fold more total tocotrienols than the unmodified parent cultivar Williams 82.

Unlike other methods used to obtain high-HGA accumulating plants, the high-HGA soybean seeds obtained using this novel approach are morphologically normal and germinate as well as the unmodified parent. Increased HGA flux in plants can be used for vitamin E biofortification and for tolerance to herbicides such as benzoylisoxazoles and P-triketones.

As disclosed herein mentioned above, the mutated allele produced in cultivar MO12 over-accumulates a central, and more importantly, limiting metabolite for vitamin E biosynthesis, namely HGA. High-HGA soybean cultivars have been produced before by co-expressing the *Erwinia herbicola* TYRA (bacterial prephenate dehydrogenase) and the *Arabidopsis* HPPD (p-hydroxyphenylpyruvate dioxygenase) in soybean (Karunanandaa et al., *Metabolic Engineering*, 7:384-400, 2005), allowing the synthesis of HGA directly from prephenate and bypassing the feed-back inhibition endogenous to HGA biosynthesis in plants. While the resulting transgenic seeds produced large amounts of HGA and a modest increase in total tocochromanol content, the high-HGA soybean cultivar produced morphologically abnormal seeds with poor germination. The plants described herein are thus superior, and provide non-transgenic alleles for conferring high-HGA in combination with normal morphology and germination.

There are numerous commercial and agronomic uses for the plants described herein. For example, a mutant HGO allele provided herein can be used for breeding efforts or transgenic manipulation for further biofortification and increased vitamin E content in soybean or other plants. For example, such plants can be transformed with transgenes encoding vitamin E biosynthetic enzymes that are known to increase the flux of vitamin E or vitamin E metabolites downstream of HGA. Also for example, such plants can be used as a genetic source of herbicide resistance. A newly discovered class of herbicides called HPPD (p-hydroxyphenylpyruvate dioxygenase) inhibitors targets HPPD, the enzyme that catalyzes the formation of HGA. Since the plants provided herein accumulates massive amounts of HGA, they can be more resistant to HPPD inhibitors such as Balance® (Bayer CropScience) or Callisto® (Syngenta).

A knock-out or knock-down of HGO genes can be done using non-transgenic methods such as irradiation mutation, as was the case with MO12, or by chemical mutagenesis. Simpler transgenic approaches, such as RNAi silencing or Zn-finger mutagenesis, involving single transgenes can also be utilized.

I. DNA MOLECULES AND PLANT TRANSFORMATION CONSTRUCTS

In one aspect, the invention provides DNA sequences encoding HGO as well as constructs for suppressing endogenous HGO expression. In one embodiment, such sequences provide a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29. Of particular interest are polynucleotide molecules wherein the polynucleotide molecules have at least about 70% sequence identity, at least about 80% sequence identity, at least about 90% sequence identity, or even greater sequence identity, specifically including about 73%, 75%, 78%, 83%, 85%, 88%, 92%, 93%, 94%, 95%, 96%, 97%, 98%, or 99% or greater sequence identity with any of such nucleotide sequences. In certain embodiments of the invention, nucleic acids hybridizing to the aforementioned sequences or a complement or reverse complement thereof, under stringent conditions, are provided. Such conditions are well known in the art, such as 1×SSC and 65° C. The invention further provides nucleic acid sequences that encode a sequence complementary to all or a part of a sequence encoding HGO gene, including an mRNA of an HGO gene, wherein the expression of the sequence in a plant is capable of down-regulating the gene in the plant. In certain embodiments of the invention, fragments or complements thereof of at least about 21, 23, 25, 28, 32, 40, 50, 100, 150, 200 or longer contiguous nucleotides of a nucleic acid sequence disclosed herein are provided that down-regulate HGO in a plant.

In a certain further embodiment, DNA constructs for plant transformation are provided. For example, a DNA construct can be for expression of an antisense RNA or dsRNA (RNAi, including siRNA and miRNA) that down-regulates HGO. Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al., (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoters such as the CaMV 35S promoter (Odell et al., *Nature*, 313:810-812, 1985), or others such as CaMV 19S (Lawton et al., *Plant Mol. Biol.* 9:315-324, 1987), nos (Ebert et al., *Proc. Natl. Acad. Sci.*, 84:5745-5749, 1987), Adh (Walker et al., *Proc. Natl. Acad. Sci. USA*, 84:6624-6628, 1987), sucrose synthase (Yang et al., *Proc. Natl. Acad. Sci. USA*, 87:4144-4148, 1990), α-tubulin, actin (Wang et al., *Molecular and Cellular Biology*, 12(8):3399-3406, 1992), cab (Sullivan et al., *Mol. Gen. Genet.*, 215(3):431-440, 1989), PEPCase (Hudspeth et al., *Plant Mol. Biol.*, 12:579-589, 1989) or those associated with the R gene complex (Chandler et al., *The Plant Cell*, 1:1175-1183, 1989). Tissue specific promoters such as root cell promoters (Conkling et al., *Plant Physiol.*, 93:1203-1211, 1990) and tissue specific enhancers (Fromm et al., *Nature*, 319:791-793, 1986) are also contemplated to be useful, as are inducible promoters such as ABA- and turgor-inducible promoters.

The DNA sequence between the transcription initiation site and the start of the coding sequence, i.e., the untranslated leader sequence, can also influence gene expression. One may thus wish to employ a particular leader sequence with a transformation construct of the invention. Leader sequences include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants may be particularly useful.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., *EMBO Journal*, 6(11):3203-3208, 1987), and is present in at least 10 other promoters (Bouchez et al., *EMBO Journal*, 8(13):4197-4204, 1989). The use of an enhancer element, such as the ocs element and particularly multiple copies of the element, may act to increase the level of transcription from adjacent promoters when applied in the context of plant transformation.

It is envisioned that sequences (or complements thereof) may be introduced under the control of novel promoters or enhancers, etc., or homologous or tissue specific promoters or control elements. Vectors for use in tissue-specific targeting of genes in transgenic plants may include tissue-specific promoters and may also include other tissue-specific control elements such as enhancer sequences. Promoters that direct specific or enhanced expression in certain plant tissues will be known to those of skill in the art in light of the present disclosure. These include, for example, the rbcS promoter, specific for green tissue; the ocs, nos and mas promoters.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. It is envisioned that the native terminator of an HGO coding sequence can be used. Alternatively, a heterologous 3' end may enhance the expression of sense or antisense HGO coding sequences and fragments. Examples of terminators include those from the nopaline synthase gene of *Agrobacterium tumefaciens* (nos 3' end), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., *Genes Dev.*, 1:1183-1200, 1987), sucrose synthase intron (Vasil et al., *Plant Physiol.*, 91:1575-1579, 1989) or TMV omega element (Gallie et al., *The Plant Cell*, 1:301-311, 1989), may further be included where desired.

C. Transit or Signal Peptides

Sequences that are joined to the coding sequence of an expressed gene, which are removed post-translationally from the initial translation product and that facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

II. Antisense and Rnai Constructs

Antisense and RNAi treatments represent one way of altering agronomic characteristics in accordance with the invention such as by down-regulation of HGO. In particular, constructs comprising an HGO coding sequence, including fragments thereof, in antisense orientation, or combinations of sense and antisense orientation, may be used to decrease or effectively eliminate the expression of an HGO gene in a plant and to alter agronomic characteristics. Accordingly, this may be used to partially or completely "knock-out" the function of an HGO gene or homologous sequences thereof.

Techniques for RNAi suppression are well known in the art and are described in, for example, Lehner et al., (*Brief Funct Genomic Proteomic*, Apr. 3(1):68-83, 2004) and Downward (BMJ, 328(7450):1245-1248, 2004). The technique is based on the fact that double stranded RNA is capable of directing the degradation of messenger RNA with sequence complementary to one or the other strand (Fire et al., *Nature*, 391: 806-11, 1998). Therefore, by expression of a particular coding sequence in sense and antisense orientation, either as a fragment or longer portion of the corresponding coding sequence, the expression of that corresponding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation or stability. Antisense and RNAi constructs, or DNA encoding such RNAs, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 17, 18, 19, 20, 21, 25, 30, 50, 75 or 100 or more contiguous nucleic acids of the nucleic acid sequence of an HGO gene, or complements thereof, which may be in sense or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that one embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have few base mismatches. For example, sequences of eighteen bases in length may be termed complementary when they have complementary nucleotides at sixteen or seventeen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. Methods for selection and design of sequences that generate RNAi are well known in the art. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

III. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., *Plant Mol. Biol.*, 21(3):415-428, 1993), by desiccation/inhibition-mediated DNA uptake (Potrykus et al., *Mol. Gen. Genet.*, 199:183-188, 1985), by electroporation (U.S. Pat. No. 5,384,253, specifically incorporated herein by reference in its entirety), by agitation with silicon carbide fibers (Kaeppler et al., *Plant Cell Reports*, 9:415-418, 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species, including biofuel crop species, may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. Another widely applicable method for delivering transforming DNA segments to plant cells is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and often, gold.

Examples of species for which have been transformed by microprojectile bombardment include monocot species such as maize (PCT Application WO 95/06128), barley (Ritala et al., *Plant Mol. Biol.*, 24(2):317-325, 1994), wheat (U.S. Pat. No. 5,563,055, specifically incorporated herein by reference in its entirety), rice (Hensgens et al., *Plant Mol. Biol.*, 22(6):1101-1127, 1993), oat (Torbet et al., *Plant Cell Reports*, 14(10):635-640, 1995; Torbet et al., *Crop Science*, 38(1):226-231, 1998), rye (Hensgens et al., *Plant Mol. Biol.*, 22(6):1101-1127, 1993), sugarcane (Bower et al., *Plant Journal*, 2:409-416. 1992), and sorghum (Casa et al., *Proc. Natl. Acad. Sci. USA*, 90(23):11212-11216, 1993); as well as a number of dicots including tobacco (Buising et al., *Mol Gen Genet*, 243(1):71-81. 1994), soybean (U.S. Pat. No. 5,322,783, specifically incorporated herein by reference in its entirety), sunflower (Knittel et al., *Plant Cell Reports*, 14(2-3):81-86, 1994), peanut (Singsit et al., *Transgenic Res.*, 6(2):169-176, 1997), cotton (McCabe et al, *Bio-Technology*, 11(5):596-598, 1993), tomato (Van Eck et al., *Plant Cell Reports*, 14(5):299-304, 1995), and legumes in general (U.S. Pat. No. 5,563,055, specifically incorporated herein by reference in its entirety).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with 10-5M abscisic acid and then transferred to growth regulator-free medium for germination.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

IV. Breeding Plants of the Invention

In addition to direct transformation of a particular plant genotype with a construct prepared according to the current invention, plants comprising a selected mutated and/or transgenic allele such as one conferring increased HGA may be made by crossing a plant having the given selected DNA to a second plant lacking the DNA. For example, an allele or locus can be introduced into a particular plant variety by crossing. Therefore, the current invention not only encompasses a plant directly mutated or transformed, but also the progeny of such plants.

As used herein the term "progeny" denotes the offspring of any generation of a parent plant prepared in accordance with the instant invention, wherein the progeny comprises a given DNA. "Crossing" a plant to provide a plant line having one or more added locus or allele relative to a starting plant line, as disclosed herein, is defined as the techniques that result in a locus or allele of the invention being introduced into a plant line by crossing a starting line with a donor plant line that comprises a locus or allele of the invention, which may or may not be transgenic in origin. To achieve this one could, for example, perform the following steps:

(a) plant seeds of the first (starting line) and second (donor plant line that comprises a locus or allele of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired locus, DNA sequence or element to a plant of a second genotype lacking the desired locus, DNA sequence or element;

(b) selecting one or more progeny plant containing the desired locus, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a locus or allele into a plant genotype is defined as the result of the process of backcross conversion. A plant genotype into which a locus or allele has been introgressed may be referred to as a backcross converted genotype, line, inbred, or hybrid. Similarly a plant genotype lacking the desired sequence may be referred to as an unconverted genotype, line, inbred, or hybrid.

V. Definitions

Down-regulation: The reduction in the expression and/or function of a given gene or product thereof relative to a control or naturally-occurring counterpart.

Expression: The combination of intracellular processes, including transcription and translation undergone by a coding DNA molecule such as a structural gene to produce a polypeptide or cause a phenotype.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an R0 transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

R0 transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

VI. Deposit Information

A deposit of soybean seeds comprising the deletion in Glyma12g20220 referred to herein was made in accordance with Budapest Treaty requirements with the American Type Culture Collection (ATCC), 10801 University Boulevard, Manassas, Va. 20110-2209 USA. The deposit is assigned ATCC Accession No. PTA-12919. The date of the deposit was May 22, 2012. Access to this deposit will be available during the pendency of the application to the Commissioner of Patents and Trademarks and persons determined by the Commissioner to be entitled thereto upon request. The deposit will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent.

EXAMPLES

Example 1

Identification and Phenotypic Characterization of a Fast Neutron-Mutagenized Soybean Plant Line (MO12).

Genotyping of a fast neutron-mutagenized soybean line (derived from cv. Williams 82) was carried out by comparative genome Hybridization (CGH). This analysis revealed one mutant (cultivar MO12) with a deletion in Glyma12g20220, a gene encoding homogentisate dioxygenase (HGO). The mutant soybean line has brown seeds, a phenotype consistent with high HGA accumulation. Conversion of accumulated HGA to tocochromanols in seeds, for example by over-expression of tocochromanol biosynthetic enzyme(s) from a seed-specific promoter, would likely dissipate the brown coloration due to oxidized HGA.

Example 2

Measurements of HGA Content in a Soybean Mutant Harboring a Deletion in Glyma12g20220.

Measurements of HGA content in soybean seeds by LC-MS showed significantly higher HGA levels in the soybean mutant harboring a deletion in Glyma12g20220 (cultivar MO12) compared to the unmodified parent line (Williams 82) (FIG. 2A). The results confirmed that HGA flux can be increased in plants through genetic manipulations to prevent the formation of functional HGA dioxygenase (HGO). Additional data were obtained showing increased HGA content in seeds, leaves and stems of cultivar MO12 as compared to unmodified Williams 82 parent.

Example 3

Measurements of HGA Content in an *Arabidopsis* Mutant Harboring a T-DNA Insertion in At5g54080.

Measurements of HGA content in seeds by LC-MS from an *Arabidopsis* mutant containing an *Agrobacterium tumefaciens*-mediated T-DNA insertion in AtSg54080 (Salk-027807), thereby disrupting HGO, showed significantly higher HGA levels as compared to the unmodified parent line (Col-O) (FIG. 2B). The results validate that HGA flux can be increased in plants through genetic manipulations to prevent the formation of functional HGA dioxygenase (HGO).

Example 4

Soybean cultivar (MO12) HGO deletion mutant herbicide resistance observations. Observations have indicated that the HGO deletion mutant (cultivar MO12) is significantly more resistant to the herbicides CALLISTO®, LAUDIS®, and IMPACT® as compared to the Williams 82 parent line. Herbicide resistance of wild-type and MO12 seedlings was evaluated in Leaf painting experiments using various concentrations of the above-mentioned herbicides (FIGS. 4, 5, and 6). Briefly, seedlings were grown until stage V1 when the unifoliate leaves were fully expanded and the emerging first trifoliate leaves were at most 1 cm long (approximately 10 days after sowing). CALLISTO® (Syngenta Crop Protection, USA), IMPACT® (IMVAC, USA) and LAUDIS® (Bayer CropScience, USA) herbicides were painted on the unifoliate leaves of V1-stage soybean seedlings using a cotton-tipped applicator. Herbicides were prepared in 1% Silwet L-77; control plants received 1% Silwet solution. Plants were observed 15 days after herbicide treatment.

Example 5

Down-Regulation of HGO in Soybean by RNA Interference or by Site-Directed DNA Sequence Modification Methods Using Nuclease Enzymes.

To repress the function of the endogenous HGO gene, vectors containing an HGO-RNAi, or an HGO-specific engineered nuclease enzyme, can be constructed and introduced into a soybean (Williams 82) by *Agrobacterium*-mediated transformation. In cases where multiple HGO genes are present, silencing or mutating these genes simultaneously can further increase HGA accumulation. To construct the RNAi vector, a nucleotide fragment of HGO is PCR-amplified from the soybean using oligonucleotide primers. The fragment is inserted into a cloning vector and transferred into an *A. tumefaciens* binary T-DNA vector by LR recombination reactions (Invitrogen, Chicago, Ill.) or directional cloning. The final binary vector is transferred into *A. tumefaciens* strain EHA105 using freezing/heat shock method or suitable transformation protocol. Soybean cultivars, wild-type with respect to HGO, can then be transformed though co-cultivation with the transgenic *A. tumefaciens* strain thereby producing a transgenic plants containing the HGO-RNAi vector. Published methodologies using engineered nuclease enzymes for targeted mutagenesis of crop plants are available, for example, for maize (Shukla et al., *Nature*, 459:437-441, 2009), rice (Li et al., *Nat Biotechnol*, 30:390-392, 2012) and soybean (Curtin et al., *Plant Physiology*, 156(2): 466-473, 2011), and could be adapted herein for other species.

Example 6

Conversion of Accumulated HGA to Tocochromanols in Soybean by Transgenic Over-Expression.

To increase the production of the various isoforms of vitamin E and their precursors, such as plastoquinones, over-expression of biosynthetic enzymes involved in tocochromanol formation can be achieved through transgenic expression in the MO12 cultivar. For example, a polynucleotide encoding HGA geranylgeranyl transferase (HGGT) can be inserted into a cloning vector under the control of a constitutive promoter and transferred into an *A. tumefaciens* binary T-DNA vector by LR recombination reactions (Invitrogen, Chicago, Ill.) or directional cloning. The final binary vector is transferred into *A. tumefaciens* strain EHA105 using freezing/heat shock method or suitable transformation protocol. Soybean cultivar MO12 can then be transformed though co-cultivation with the transgenic *A. tumefaciens* strain thereby producing a transgenic MO12 cultivar containing the HGGT expression vector.

Transgenic lines can be identified through PCR analysis and used for further analyses. Quantitative real-time PCR analysis of transgenic lines can indicate which lines have their HGO transcript effectively down-regulated when compared to the empty vector control line.

Southern blot hybridization analysis can confirm that the transgene is stably integrated in the soybean genome and that the regenerated positive lines are truly independent transformants. Both single copy and multiple copy integrations of the transgene can be observed in the transgenic lines. Increased HGA content of the HGO-RNAi transgenic soybean plants can be analyzed by LC-MS.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A plant comprising a mutated Glyma12g20220 allele, a representative sample of seed comprising said mutated allele having been deposited under ATCC Accession No. PTA-12919.

2. The plant of claim 1, further comprising a transgene that encodes an enzyme catalyzing at least one step in tocopherol biosynthesis.

3. The plant of claim 2, wherein the enzyme is selected from the group consisting of: MT1, tMT2, GMT, tyrA, HPT, tocopherol cyclase, chlorophyllase, dxs, dxr, GGPPS, AANT1, LTT1, IDI, GGH, HGGT, and HST.

4. A plant part of the plant of claim 1.

5. The plant part of claim 4, further defined as a protoplast, cell, meristem, root, pistil, anther, flower, seed, embryo, stalk or petiole.

6. A seed that produces the plant of claim 1.

7. A method of increasing production of homogentisic acid (HGA) or a metabolic product derived therefrom in a plant comprising down-regulating homogentisic acid dioxygenase (HGO) in the plant relative to a wild-type plant, wherein the plant comprises a mutated Glyma12g20220 allele, a representative sample of seed comprising said mutated allele having been deposited under ATCC Accession No. PTA-12919, and wherein said down-regulating comprises introgressing into the plant the mutated Glyma12g20220 allele.

8. The method of claim 7, further comprising expressing in the plant a transgene that encodes an enzyme catalyzing at least one step in tocopherol biosynthesis.

9. The method of claim 8, wherein the enzyme is selected from the group consisting of: MT1, tMT2, GMT, tyrA, HPT, tocopherol cyclase, chlorophyllase, dxs, dxr, GGPPS, AANT1, LTT1, IDI, GGH, HGGT, and HST.

10. A method for producing a commercial product comprising obtaining a plant of claim 1 or a part thereof and producing a commercial product therefrom.

11. The method of claim 10, wherein the commercial product is protein concentrate, protein isolate, grain, soybean hulls, meal, flour or oil.

12. A method of increasing tolerance to an herbicidal inhibitor of ρ-hydroxyphenylpyruvate dioxygenase (HPPD) in a plant comprising down-regulating homogentisic acid dioxygenase (HGO) in the plant relative to a wild-type plant, wherein the plant comprises increased tolerance to an herbicidal inhibitor of ρ-hydroxyphenylpyruvate dioxygenase (HPPD) and produces seeds comprising normal germination relative to a wild type plant, wherein said down-regulating comprises introgressing into the plant a mutated Glyma12g20220 allele;
obtaining a plurality of plants with down-regulated HGO; and
selecting from the plurality of plants a plant exhibiting an increased level of herbicide tolerance relative to the wild-type plant.

* * * * *

SEQUENCE LISTING

<160> NUMBER OF SEQ ID NOS: 29

<210> SEQ ID NO 1
<211> LENGTH: 1766
<212> TYPE: DNA

<213> ORGANISM: Glycine Max

<400> SEQUENCE: 1

```
aaactttgtg ttcactcttt ctcttttttg gtgttagttc ggtgaatcat ggagaaccca      60
atcgacggtg gcgagttcgt gtacctttcc gggttcggca accacttctc ctccgaggcc     120
ctcgccggag ctctgccggt ggcgcagaac agccccctcg tctgcccgta cggcctctac     180
gccgagcaaa tctctggcac ctccttcacc tcccctcgca accgcaacct cttcagttgg     240
ttttatcgga tcaagccatc ggtgactcac gaaccgttca agcctagggt acctggtaat     300
ggcagaattt tgagtgagtt taacaactcc aacagttctg ctaacccaac tcagcttaga     360
tggaagccct tggatgcgcc cgattcgcca acagatttca ttgatgggtt gtccactgtg     420
tgtggttctg gcagctcctt catgcgccac ggatatgcta ttcacatgta cactgccaac     480
aaatcaatgg acaattgtgc cttttgcaat gctgatggtg acttcttgat agttccccaa     540
caaggaagac tccttgtcac tactgaatgt ggaaggttga agtttctccc aggtgaaatt     600
gctatattac ctcaaggctt tcgtttttct gtgaatcttc ctgatggtcc atcccgtggt     660
tatgttgctg aaatttttgg tactcatttt caacttcctg atctgggacc aataggtgct     720
aatggccttg cttcccctag ggatttcctt gttcccactg cttggtttga agataaatct     780
tatcctgggt acaccatagt gcagaaattt ggtggtgagc tctttgatgc agtacaagat     840
ttctctcctt tcaatgttgt tgcttggcat ggtaattatg ttccatatat gtatgattta     900
aacaaattct gcccttataa tacagttctg tttgatcata gtgatccatc aatcaatact     960
gtgttgacag caccaactga taaacctgga gtggcattgc ttgattttgt cattttccca    1020
cccagatggc tggttgctga gcatactttc cggcctccat attatcatcg caattgcatg    1080
agtgaattta tgggcctcat tcatggtggt tatgaggcca aggctgatgg atttcttccc    1140
ggtggtgcaa gtctccatag ttgtatgact ccccatggtc ctgataccaa gtcatatgag    1200
gctaccattg cacgaggaaa tgatgtagga ccttgcaaga tcactgacac aatggcttt     1260
atgtttgaat cgagtttgat accccgtatc agtcaatggg cctcagaatc accgttcttg    1320
gaccaagatt attaccagtg ttggattggc ctgaaatctc attttgcagt tactaagacg    1380
tctcctgaaa acccaagctt gggaaatgga gattgaggag tgaaatgggt gttgcgacac    1440
aggcagttag accaccaaaa gattgggttt ctttgtacat aaaaataaat gtaattacaa    1500
aaatataatt taggtgtgtc aaaagtgaac tcaacccaat tggtgggaat caaatggttt    1560
caggcaagtt ttatgtacag tgcaagggac tggaatcttt aagatctgtc ctaaagaggg    1620
tctgtgttaa tcacaatcta taagttaggt tgtttttggt tgtgcgttat tttcatgcag    1680
gattcctaag aagtaggagc tcataacttt tgatttaaca atcatttgaa atcttccaac    1740
ggaaaacaaa cacgtactta gagata                                         1766
```

<210> SEQ ID NO 2
<211> LENGTH: 455
<212> TYPE: PRT
<213> ORGANISM: Glycine max

<400> SEQUENCE: 2

```
Met Glu Asn Pro Ile Asp Gly Gly Glu Phe Val Tyr Leu Ser Gly Phe
  1               5                  10                  15

Gly Asn His Phe Ser Ser Glu Ala Leu Ala Gly Ala Leu Pro Val Ala
             20                  25                  30

Gln Asn Ser Pro Leu Val Cys Pro Tyr Gly Leu Tyr Ala Glu Gln Ile
```

```
                35                  40                  45
Ser Gly Thr Ser Phe Thr Ser Pro Arg Asn Arg Asn Leu Phe Ser Trp
 50                  55                  60

Phe Tyr Arg Ile Lys Pro Ser Val Thr His Glu Pro Phe Lys Pro Arg
 65                  70                  75                  80

Val Pro Gly Asn Gly Arg Ile Leu Ser Glu Phe Asn Asn Ser Asn Ser
                 85                  90                  95

Ser Ala Asn Pro Thr Gln Leu Arg Trp Lys Pro Leu Asp Ala Pro Asp
                100                 105                 110

Ser Pro Thr Asp Phe Ile Asp Gly Leu Ser Thr Val Cys Gly Ser Gly
                115                 120                 125

Ser Ser Phe Met Arg His Gly Tyr Ala Ile His Met Tyr Thr Ala Asn
130                 135                 140

Lys Ser Met Asp Asn Cys Ala Phe Cys Asn Ala Asp Gly Asp Phe Leu
145                 150                 155                 160

Ile Val Pro Gln Gln Gly Arg Leu Leu Val Thr Thr Glu Cys Gly Arg
                165                 170                 175

Leu Lys Val Ser Pro Gly Glu Ile Ala Ile Leu Pro Gln Gly Phe Arg
                180                 185                 190

Phe Ser Val Asn Leu Pro Asp Gly Pro Ser Arg Gly Tyr Val Ala Glu
                195                 200                 205

Ile Phe Gly Thr His Phe Gln Leu Pro Asp Leu Gly Pro Ile Gly Ala
210                 215                 220

Asn Gly Leu Ala Ser Pro Arg Asp Phe Leu Val Pro Thr Ala Trp Phe
225                 230                 235                 240

Glu Asp Lys Ser Tyr Pro Gly Tyr Thr Ile Val Gln Lys Phe Gly Gly
                245                 250                 255

Glu Leu Phe Asp Ala Val Gln Asp Phe Ser Pro Phe Asn Val Val Ala
                260                 265                 270

Trp His Gly Asn Tyr Val Pro Tyr Met Tyr Asp Leu Asn Lys Phe Cys
                275                 280                 285

Pro Tyr Asn Thr Val Leu Phe Asp His Ser Asp Pro Ser Ile Asn Thr
290                 295                 300

Val Leu Thr Ala Pro Thr Asp Lys Pro Gly Val Ala Leu Leu Asp Phe
305                 310                 315                 320

Val Ile Phe Pro Pro Arg Trp Leu Val Ala Glu His Thr Phe Arg Pro
                325                 330                 335

Pro Tyr Tyr His Arg Asn Cys Met Ser Glu Phe Met Gly Leu Ile His
                340                 345                 350

Gly Gly Tyr Glu Ala Lys Ala Asp Gly Phe Leu Pro Gly Gly Ala Ser
                355                 360                 365

Leu His Ser Cys Met Thr Pro His Gly Pro Asp Thr Lys Ser Tyr Glu
370                 375                 380

Ala Thr Ile Ala Arg Gly Asn Asp Val Gly Pro Cys Lys Ile Thr Asp
385                 390                 395                 400

Thr Met Ala Phe Met Phe Glu Ser Ser Leu Ile Pro Arg Ile Ser Gln
                405                 410                 415

Trp Ala Ser Glu Ser Pro Phe Leu Asp Gln Asp Tyr Tyr Gln Cys Trp
                420                 425                 430

Ile Gly Leu Lys Ser His Phe Ala Val Thr Lys Thr Ser Pro Glu Asn
                435                 440                 445

Pro Ser Leu Gly Asn Gly Asp
450                 455
```

<210> SEQ ID NO 3
<211> LENGTH: 1467
<212> TYPE: DNA
<213> ORGANISM: Glycine max

<400> SEQUENCE: 3

| | |
|---|---:|
| atggcgaacc caatcgacgg tggcgagttc gagtgccttt ccgggttcgg caaccacttc | 60 |
| tcctccgagg ccctcgccgg agctctgccg gcggcgcaga acagccccct cgtctgcccg | 120 |
| tacggactat acgccgagca aatctccggc acctccttca cttctcctcg caaccgcaac | 180 |
| ctcttcagtt ggttttatcg gatcaaacca tcagtgactc acgaaccgtt caagccaaga | 240 |
| gtaccgggta atggaggat tttgagtgag ttcaacaact ccagcagttc tgctaaccca | 300 |
| actcagctta gatggaagcc catggatgca cccgattcgc caatggattt cattgatggg | 360 |
| ttgtccacca tgtgtggttc tggcagctcc ttcatgcgcc acggatatgc tattcacatg | 420 |
| tacaatgcca acaaatcaat ggacaattgt gccttttgca atgctgatgg tgacttcttg | 480 |
| atagttcccc aacaaggaag actccttatc actactgaat gtggaagatt gaaagtttct | 540 |
| ccgggtgaaa ttgctataat acctcacggt tttcgttttt ctgtgaatct gcctgatggt | 600 |
| ccatcccgcg gttatgttgc tgaaattttt ggtactcatt tcaacttcc tgatctggga | 660 |
| ccaataggtg ctaatggtct tgcttcccca agggatttcc ttgttcctag tgcttggttt | 720 |
| gaagataaat cttatcctgg gtacaccata gtgcagaagt ttggtggtga actctttgat | 780 |
| gcagtgggtg ttttcccctt cttcattgtg agttatgatt acaatcatat tctgtttgat | 840 |
| catagtgatc catcaatcaa tactgtgttg accgcaccaa ctgataaacc tggagtggca | 900 |
| ttgcttgatt ttgtcatttt tccacccaga tggctggttg ctgagcatac tttccggcct | 960 |
| ccatattatc atcgcaattg catgagtgaa tttatgggcc ttattcatgg tggctatgag | 1020 |
| gccaaggctg atggatttct tcccggtggt gcaagtctcc ataattgtat gactccccat | 1080 |
| ggtcctgata caaagtcata tgaggctacc attgcacgag gaaatgatgg aggaccttgt | 1140 |
| aagatcacgg acacaatggc ttttatgttt gaatcgagtt tgatacccg tatcagtcaa | 1200 |
| tgggccctgg aatcaccgtt cttggatcaa gattattacc aatgttggat tggcctgaaa | 1260 |
| tctcattttta cagttactga gacatctcct gaaaacacga acttgcggaa tggacagtga | 1320 |
| ggagtgaaat gggtgttaaa agtgaactca accaaaagat tgtggaatgg acaattagac | 1380 |
| caccaaaaga ttgggttgtt ttgtacatgt aattaaagaa atataatcaa gtttaatgtt | 1440 |
| tatatactaa atattggaaa ataattt | 1467 |

<210> SEQ ID NO 4
<211> LENGTH: 343
<212> TYPE: PRT
<213> ORGANISM: Glycine max

<400> SEQUENCE: 4

```
Met Ala Asn Pro Ile Asp Gly Gly Glu Phe Glu Cys Leu Ser Gly Phe
1               5                   10                  15

Gly Asn His Phe Ser Ser Glu Ala Leu Ala Gly Ala Leu Pro Ala Ala
            20                  25                  30

Gln Asn Ser Pro Leu Val Cys Pro Tyr Gly Leu Tyr Ala Glu Gln Ile
        35                  40                  45

Ser Gly Thr Ser Phe Thr Ser Pro Arg Asn Arg Asn Leu Phe Ser Trp
    50                  55                  60
```

```
Phe Tyr Arg Ile Lys Pro Ser Val Thr His Glu Pro Phe Lys Pro Arg
 65                  70                  75                  80

Val Pro Gly Asn Gly Arg Ile Leu Ser Glu Phe Asn Asn Ser Ser Ser
                 85                  90                  95

Ser Ala Asn Pro Thr Gln Leu Arg Trp Lys Pro Met Asp Ala Pro Asp
            100                 105                 110

Ser Pro Met Asp Phe Ile Asp Gly Leu Ser Thr Met Cys Gly Ser Gly
        115                 120                 125

Ser Ser Phe Met Arg His Gly Tyr Ala Ile His Met Tyr Asn Ala Asn
    130                 135                 140

Lys Ser Met Asp Asn Cys Ala Phe Cys Asn Ala Asp Gly Asp Phe Leu
145                 150                 155                 160

Ile Val Pro Gln Gln Gly Arg Leu Leu Ile Thr Thr Glu Cys Gly Arg
                165                 170                 175

Leu Lys Val Ser Pro Gly Glu Ile Ala Ile Pro His Gly Phe Arg
            180                 185                 190

Phe Ser Val Asn Leu Pro Asp Gly Pro Ser Arg Gly Tyr Val Ala Glu
        195                 200                 205

Ile Phe Gly Thr His Phe Gln Leu Pro Asp Leu Gly Pro Ile Gly Ala
    210                 215                 220

Asn Gly Leu Ala Ser Pro Arg Asp Phe Leu Val Pro Ser Ala Trp Phe
225                 230                 235                 240

Glu Asp Lys Ser Tyr Pro Gly Tyr Thr Ile Val Gln Lys Phe Gly Gly
                245                 250                 255

Glu Leu Phe Asp Ala Val Gly Val Phe Pro Phe Phe Ile Val Ser Tyr
            260                 265                 270

Asp Tyr Asn His Ile Leu Phe Asp His Ser Asp Pro Ser Ile Asn Thr
        275                 280                 285

Val Leu Thr Ala Pro Thr Asp Lys Pro Gly Val Ala Leu Leu Asp Phe
    290                 295                 300

Val Ile Phe Pro Pro Arg Trp Leu Val Ala Glu His Thr Phe Arg Pro
305                 310                 315                 320

Pro Tyr Tyr His Arg Asn Cys Met Ser Glu Phe Met Gly Leu Ile His
                325                 330                 335

Gly Gly Tyr Glu Ala Lys Ala
            340

<210> SEQ ID NO 5
<211> LENGTH: 737
<212> TYPE: DNA
<213> ORGANISM: Glycine max

<400> SEQUENCE: 5
atgggaaaat attatatcac ttataggtac aatgccaaca atcaatgga caattgtgcc      60 ttttgcaatg ctgatggtga cttcttgata gttccccaac aaggaagact ccttatcact    120
actgaatgtg gaagattgaa agtttctccg ggtgaaattg ctataatacc tcacggtttt    180
cgttttcctg tgaatctgcc tgatggtcca tcccgcggtt atgttgctga aattttggt    240 actcattttc aacttcctga tctgggacca ataggtgcta atggtcttgc ttccccaagg    300
gatttccttg ttcctactgc ttggtttgaa gataaatctt atcctgggta caccatagtg    360
cagaagtttg gtggtgaact ctttgatgca gtacaagatt tctctccctt caatgttgtt    420
gcttggcatg gtaattatta tgatttaagc aaattctgcc cttataatac agttctgttt    480
gatcatagtg acccatctat caatactgtg ttgaccgcac caactgataa acctggagtg    540
```

```
gcattgcttg attttgtcat tttcccaccc agatggctgg ttgctgagca tactttcctt    600
cctccatatt atcatcgcaa ttgcatgagt gaatttatgg gccttattca tggtggctat    660
gaggccaacg ctgatggatt tcttcccggt ggtgcaagtc tccataattg tatgactccc    720
catggtcctg atacaaa                                                   737
```

```
<210> SEQ ID NO 6
<211> LENGTH: 245
<212> TYPE: PRT
<213> ORGANISM: Glycine max

<400> SEQUENCE: 6

Met Gly Lys Tyr Tyr Ile Thr Tyr Arg Tyr Asn Ala Asn Lys Ser Met
1               5                   10                  15

Asp Asn Cys Ala Phe Cys Asn Ala Asp Gly Asp Phe Leu Ile Val Pro
            20                  25                  30

Gln Gln Gly Arg Leu Leu Ile Thr Thr Glu Cys Gly Arg Leu Lys Val
        35                  40                  45

Ser Pro Gly Glu Ile Ala Ile Ile Pro His Gly Phe Arg Phe Ser Val
    50                  55                  60

Asn Leu Pro Asp Gly Pro Ser Arg Gly Tyr Val Ala Glu Ile Phe Gly
65                  70                  75                  80

Thr His Phe Gln Leu Pro Asp Leu Gly Pro Ile Gly Ala Asn Gly Leu
                85                  90                  95

Ala Ser Pro Arg Asp Phe Leu Val Pro Thr Ala Trp Phe Glu Asp Lys
            100                 105                 110

Ser Tyr Pro Gly Tyr Thr Ile Val Gln Lys Phe Gly Gly Glu Leu Phe
        115                 120                 125

Asp Ala Val Gln Asp Phe Ser Pro Phe Asn Val Val Ala Trp His Gly
    130                 135                 140

Asn Tyr Asp Leu Ser Lys Phe Cys Pro Tyr Asn Thr Val Leu Phe
145                 150                 155                 160

Asp His Ser Asp Pro Ser Ile Asn Thr Val Leu Thr Ala Pro Thr Asp
                165                 170                 175

Lys Pro Gly Val Ala Leu Leu Asp Phe Val Ile Phe Pro Pro Arg Trp
            180                 185                 190

Leu Val Ala Glu His Thr Phe Leu Pro Pro Tyr Tyr His Arg Asn Cys
        195                 200                 205

Met Ser Glu Phe Met Gly Leu Ile His Gly Gly Tyr Glu Ala Asn Ala
    210                 215                 220

Asp Gly Phe Leu Pro Gly Gly Ala Ser Leu His Asn Cys Met Thr Pro
225                 230                 235                 240

His Gly Pro Asp Thr
                245
```

```
<210> SEQ ID NO 7
<211> LENGTH: 2203
<212> TYPE: DNA
<213> ORGANISM: Oryza sativa

<400> SEQUENCE: 7
ggagttgcga aaattgttgt gttgtaataa gcaaacgtct tgcaacaata ctcctccccc    60
taataggaga ggctaataca gaacaaattt tctttagaag agggtaaaag tatattgata   120
aagaagagat gctaatacat agaatatgtg ttagtaatca gtattagatt actactagta   180
```

-continued

| | |
|---|---|
| tgtagtagta atatgagaga gtaattatta ttatttttat ttaggaggag tagttgattg | 240 |
| gaggatatat acagacggtg agaagaagag tgagatacag gagaggagaa gcctcctgaa | 300 |
| actgaaagga gacaagcagt tgtgttgtcc ttctccctct cctccggcca gcggccatgg | 360 |
| ccatggcaac ggcaaccccc gcggcgcaga atgagcagca ggagaagggg gggttggagt | 420 |
| acgtatatct gtcggggctg ggcaacagct tgtcgtcgga ggcggtggcg gggacgctcc | 480 |
| cgcgcgggca gaacagcccg ctggtctgcc gctgggact ctacgccgag cagctctccg | 540 |
| gcacgccctt caccgccccg cgcgcccgca acctccgaac atggctgtac cggatcaagc | 600 |
| cttcggtgac ccacgagccc ttccaccccc gtcgccccgc ccaccccgc ctcattgggg | 660 |
| atttcgaccg caccaccacc gacaccgtcg ccacgcccac ccagctgcgc tggcgccccg | 720 |
| ccgacgtgcc cccccaccat cctccctcg atttcatcga tggcctctac accgtctgcg | 780 |
| gcgctggcag ctccttcctg cgccacggat acgccatcca catgtacgct gctaacaagt | 840 |
| ccatggacgg atgcgccttt tgcaacgctg acggcgattt cctcattgtc cccagcaag | 900 |
| gaaagctgtt gatcacaact gaatgtggga agctgctagt cccacctggt gaaattgttg | 960 |
| tcattcccca gggttttcgc tttgctgttg atttgcccga tggtccttca cgtggctatg | 1020 |
| tttctgagat tttcggtacc cactttcagc tccctgatct tggcccgatt ggtgcaaatg | 1080 |
| gcttggcttc ggcaagggat tccctttccc caacagcatg gtttgagcaa gtccaccgcc | 1140 |
| caggatacac aattgtgcag aaatatggtg gtgagctatt cactgccact caggactttt | 1200 |
| ctccatttaa tgtggtagcg tggcatggaa attatgtccc ttacaagtac gacctgagta | 1260 |
| aattctgtcc atttaacact gttctattcg atcatgctga tccatcagta aatacagtgc | 1320 |
| tgactgcacc aactgataag cctggtgtcg cattgcttga ttttgtgata ttcccgccta | 1380 |
| gatggttggt cgctgagaac acatttcgcc ctccatacta tcatcgcaat tgcatgagtg | 1440 |
| aatttatggg attgatctat ggaatatacg aggccaaagc tgatggtttt cttcctggag | 1500 |
| gtgctagcct tcacagttgc atgacacctc atggcccaga caccaagaca tacgaggcaa | 1560 |
| caatcagccg tcctgatgcc aatgagccat caaggctaag cggcacgctt gcattcatgt | 1620 |
| tcgagtctgc actcatcccc agggtttgcc aatgggccct cgattcccca tcccgggatc | 1680 |
| tcgattacta ccagtgctgg attggattga atcccacttc ctcacatgac aatggagggg | 1740 |
| caaccagcga agaaccatgc agaaagtagc tttgatcagt tttagtagct tatgatgctg | 1800 |
| tgcttgtgta tattttgtga ggctgtaact gaaccattca ccagatccgt gtaagtaaag | 1860 |
| acaataatgc tcagcagcct gtactgtaca atcgtgggta tagcattatc agaagcaaga | 1920 |
| atgtcaattt caataagagg ttgcctacac tgtaggcaga ttagtacagg cgtgtttgta | 1980 |
| acaccatgaa tgaatgaatg gatggatgga caccgtgtga ggtaccatta acatgccgcc | 2040 |
| ggaaagaaga tgttacattc gcaacttggg actgttaaca tgttcccctc tgttgagata | 2100 |
| cagattgatg tggggagttg agatagataa aattgatcta ttttggtttt ggttttggac | 2160 |
| ctatgatata ataattggtt tggtgtttag agcggaacct gtc | 2203 |

<210> SEQ ID NO 8
<211> LENGTH: 470
<212> TYPE: PRT
<213> ORGANISM: Oryza sativa

<400> SEQUENCE: 8

Met Ala Met Ala Thr Ala Thr Pro Ala Ala Gln Asn Glu Gln Gln Glu
1               5                   10                  15

Lys Gly Gly Leu Glu Tyr Val Tyr Leu Ser Gly Leu Gly Asn Ser Leu
                20                  25                  30

Ser Ser Glu Ala Val Ala Gly Thr Leu Pro Arg Gly Gln Asn Ser Pro
            35                  40                  45

Leu Val Cys Pro Leu Gly Leu Tyr Ala Glu Gln Leu Ser Gly Thr Pro
        50                  55                  60

Phe Thr Ala Pro Arg Ala Arg Asn Leu Arg Thr Trp Leu Tyr Arg Ile
65                  70                  75                  80

Lys Pro Ser Val Thr His Glu Pro Phe His Pro Arg Arg Pro Ala His
                85                  90                  95

Pro Arg Leu Ile Gly Asp Phe Asp Arg Thr Thr Thr Asp Thr Val Ala
            100                 105                 110

Thr Pro Thr Gln Leu Arg Trp Arg Pro Ala Asp Val Pro Pro His His
        115                 120                 125

Pro Pro Leu Asp Phe Ile Asp Gly Leu Tyr Thr Val Cys Gly Ala Gly
    130                 135                 140

Ser Ser Phe Leu Arg His Gly Tyr Ala Ile His Met Tyr Ala Ala Asn
145                 150                 155                 160

Lys Ser Met Asp Gly Cys Ala Phe Cys Asn Ala Asp Gly Asp Phe Leu
                165                 170                 175

Ile Val Pro Gln Gln Gly Lys Leu Leu Ile Thr Thr Glu Cys Gly Lys
            180                 185                 190

Leu Leu Val Pro Pro Gly Glu Ile Val Ile Pro Gln Gly Phe Arg
        195                 200                 205

Phe Ala Val Asp Leu Pro Asp Gly Pro Ser Arg Gly Tyr Val Ser Glu
    210                 215                 220

Ile Phe Gly Thr His Phe Gln Leu Pro Asp Leu Gly Pro Ile Gly Ala
225                 230                 235                 240

Asn Gly Leu Ala Ser Ala Arg Asp Phe Leu Ser Pro Thr Ala Trp Phe
                245                 250                 255

Glu Gln Val His Arg Pro Gly Tyr Thr Ile Val Gln Lys Tyr Gly Gly
            260                 265                 270

Glu Leu Phe Thr Ala Thr Gln Asp Phe Ser Pro Phe Asn Val Val Ala
        275                 280                 285

Trp His Gly Asn Tyr Val Pro Tyr Lys Tyr Asp Leu Ser Lys Phe Cys
    290                 295                 300

Pro Phe Asn Thr Val Leu Phe Asp His Ala Asp Pro Ser Val Asn Thr
305                 310                 315                 320

Val Leu Thr Ala Pro Thr Asp Lys Pro Gly Val Ala Leu Leu Asp Phe
                325                 330                 335

Val Ile Phe Pro Pro Arg Trp Leu Val Ala Glu Asn Thr Phe Arg Pro
            340                 345                 350

Pro Tyr Tyr His Arg Asn Cys Met Ser Glu Phe Met Gly Leu Ile Tyr
        355                 360                 365

Gly Ile Tyr Glu Ala Lys Ala Asp Gly Phe Leu Pro Gly Gly Ala Ser
    370                 375                 380

Leu His Ser Cys Met Thr Pro His Gly Pro Asp Thr Lys Thr Tyr Glu
385                 390                 395                 400

Ala Thr Ile Ser Arg Pro Asp Ala Asn Glu Pro Ser Arg Leu Ser Gly
                405                 410                 415

Thr Leu Ala Phe Met Phe Glu Ser Ala Leu Ile Pro Arg Val Cys Gln
            420                 425                 430

Trp Ala Leu Asp Ser Pro Ser Arg Asp Leu Asp Tyr Tyr Gln Cys Trp

```
                435             440             445
Ile Gly Leu Lys Ser His Phe Ser His Asp Asn Gly Gly Ala Thr Ser
    450                 455                 460

Glu Glu Pro Cys Arg Lys
465                 470

<210> SEQ ID NO 9
<211> LENGTH: 470
<212> TYPE: PRT
<213> ORGANISM: Oryza sativa

<400> SEQUENCE: 9

Met Ala Met Ala Thr Ala Thr Pro Ala Ala Gln Asn Glu Gln Gln Glu
1               5                   10                  15

Lys Gly Gly Leu Glu Tyr Val Tyr Leu Ser Gly Leu Gly Asn Ser Leu
            20                  25                  30

Ser Ser Glu Ala Val Ala Gly Thr Leu Pro Arg Gly Gln Asn Ser Pro
        35                  40                  45

Leu Val Cys Pro Leu Gly Leu Tyr Ala Glu Gln Leu Ser Gly Thr Pro
    50                  55                  60

Phe Thr Ala Pro Arg Ala Arg Asn Leu Arg Thr Trp Leu Tyr Arg Ile
65                  70                  75                  80

Lys Pro Ser Val Thr His Glu Pro Phe His Pro Arg Arg Pro Ala His
                85                  90                  95

Pro Arg Leu Ile Gly Asp Phe Asp Arg Thr Thr Thr Asp Thr Val Ala
            100                 105                 110

Thr Pro Thr Gln Leu Arg Trp Arg Pro Ala Asp Val Pro Pro His His
        115                 120                 125

Pro Pro Leu Asp Phe Ile Asp Gly Leu Tyr Thr Val Cys Gly Ala Gly
    130                 135                 140

Ser Ser Phe Leu Arg His Gly Tyr Ala Ile His Met Tyr Ala Ala Asn
145                 150                 155                 160

Lys Ser Met Asp Gly Cys Ala Phe Cys Asn Ala Asp Gly Asp Phe Leu
                165                 170                 175

Ile Val Pro Gln Gln Gly Lys Leu Leu Ile Thr Thr Glu Cys Gly Lys
            180                 185                 190

Leu Leu Val Pro Pro Gly Glu Ile Val Ile Pro Gln Gly Phe Arg
        195                 200                 205

Phe Ala Val Asp Leu Pro Asp Gly Pro Ser Arg Gly Tyr Val Ser Glu
    210                 215                 220

Ile Phe Gly Thr His Phe Gln Leu Pro Asp Leu Gly Pro Ile Gly Ala
225                 230                 235                 240

Asn Gly Leu Ala Ser Ala Arg Asp Phe Leu Ser Pro Thr Ala Trp Phe
                245                 250                 255

Glu Gln Val His Arg Pro Gly Tyr Thr Ile Val Gln Lys Tyr Gly Gly
            260                 265                 270

Glu Leu Phe Thr Ala Thr Gln Asp Phe Ser Pro Phe Asn Val Val Ala
        275                 280                 285

Trp His Gly Asn Tyr Val Pro Tyr Lys Tyr Asp Leu Ser Lys Phe Cys
    290                 295                 300

Pro Phe Asn Thr Val Leu Phe Asp His Ala Asp Pro Ser Val Asn Thr
305                 310                 315                 320

Val Leu Thr Ala Pro Thr Asp Lys Pro Gly Val Ala Leu Leu Asp Phe
                325                 330                 335
```

```
Val Ile Phe Pro Pro Arg Trp Leu Val Ala Glu Asn Thr Phe Arg Pro
            340                 345                 350

Pro Tyr Tyr His Arg Asn Cys Met Ser Glu Phe Met Gly Leu Ile Tyr
        355                 360                 365

Gly Ile Tyr Glu Ala Lys Ala Asp Gly Phe Leu Pro Gly Gly Ala Ser
    370                 375                 380

Leu His Ser Cys Met Thr Pro His Gly Pro Asp Thr Lys Thr Tyr Glu
385                 390                 395                 400

Ala Thr Ile Ser Arg Ala Asp Ala Asn Glu Pro Ser Arg Leu Ser Gly
                405                 410                 415

Thr Leu Ala Phe Met Phe Glu Ser Ala Leu Ile Pro Arg Val Cys Gln
                420                 425                 430

Trp Ala Leu Asp Ser Pro Ser Arg Asp Leu Asp Tyr Tyr Gln Cys Trp
            435                 440                 445

Ile Gly Leu Lys Ser His Phe Ser His Asp Asn Gly Gly Ala Thr Ser
    450                 455                 460

Glu Glu Pro Cys Arg Lys
465                 470

<210> SEQ ID NO 10
<211> LENGTH: 1757
<212> TYPE: DNA
<213> ORGANISM: Zea mays

<400> SEQUENCE: 10
aggaggcaag tcgtgccgtg ccgtctgctc cttgcctgct ctgctggtct cgccgttgcc    60
ggcttgcccc gtccgtgcgt ccatctgttt cctccttgga tcctcgacaa gcaatggcca   120
tggaggagga gcagacacca cccgagctgc gctacctctc gggcctgggc aacacccttc   180
cgtcggaggc ggtgccgggg tcgctccccg tggggcagaa caacccgcta gtgtgcccgc   240
tgggactcta cgccgagcag ctctccggca cctccttcac caccccgcgc gcccggaacc   300
tgcgcacgtg gctgtaccgg atcaagccgt cggtgaccca cgaacccttc tatccgcgga   360
accccaccaa cgagcgcctc gtcggcgagt cgaccgcac caccaccgtc gccacgccca   420
cgcagctgcg ctggaggccc gccgacgtgc cctccaccc gggcctcgac ttcatcgacg   480
gactctacac cgtctgcggc gccggcagct catgcctccg acacggatac gccatccaca   540
tgtatgctgc taacaagccc atggatggat gctccttgtg caatgcggac ggtgacttcc   600
tcattgttcc ccagcaagga aggttattta tcacaaccga gtgcggaagg ctgctggttt   660
cacccggcga gatcgtcgtg atccctcaag gtctgtcgac ttgccggatg   720 gccccctcgcg tggctatgtc tctgagatct tcggcgccca ttttcagctc cctgatcttg   780
gcccaattgg tgccaatggc ttggcttcgc cgagggattt cctttccccg acagcatggt   840
ttgagcagga gcaccaccct ggatacacaa tagtgcacaa gtatggtggc gagctgttca   900
gcgccacgca ggatttctct ccattcaacg tggtcgcgtg gcatgggaat tatgtccctt   960
acaagtatga tctgagtaag ttctgtccat tcaacaccgt cctcttggat catggcgacc  1020
cgtcagtgaa cacagttcta actgcgccaa ctgataagcc tggcgtcgcg ttgcttgatt  1080
ttgtaatatt cccacccaga tggctggttg ctgagaatac attccgccca ccctactacc  1140
accgcaactg catgagcgaa ttcatgggcc tcatctatgg gattggcagc agtcatgtga  1200
agagatgtaa agacgatgca catctgcagg ctaaggccga tggttttctt cctggtggcg  1260
ccagccttca cagctgcatg acaccgcatg ggccagacac caagacgtac gaggcaacga  1320
```

```
tcagccgtgc tgctgccaac gagccatcca ggctcagtgg tacgttggcg ttcatgtttg    1380
agtcttggct tatccctcgc gtgtgcccat gggctctgga ttccccgtgt cgggacctcg    1440
actactacca gtgctggatc ggattgaagt cacacttttc acctcctgct gctgctgttg    1500
atgatgagaa cgagtagctg cttacagcag cagtcttgga acggacaggc agcgaactga    1560
aactggggtg gatatgctgt acgtcgtgtc ctgcttgctg tcggtttctg aagcttttag    1620
ctggcaggga caggcggctg ttggctttgc tgattgccca accctctcct gtaatattaa    1680
tcctaccaga gaaacttaaa cttgactcaa ccgatatgct attaaataaa taaagcaagc    1740
aagttaggat acgagtt                                                   1757
```

<210> SEQ ID NO 11
<211> LENGTH: 467
<212> TYPE: PRT
<213> ORGANISM: Zea mays

<400> SEQUENCE: 11

```
Met Ala Met Glu Glu Gln Thr Pro Pro Glu Leu Arg Tyr Leu Ser
1               5                   10                  15

Gly Leu Gly Asn Thr Phe Thr Ser Glu Ala Val Pro Gly Ser Leu Pro
            20                  25                  30

Val Gly Gln Asn Asn Pro Leu Val Cys Pro Leu Gly Leu Tyr Ala Glu
        35                  40                  45

Gln Leu Ser Gly Thr Ser Phe Thr Thr Pro Arg Ala Arg Asn Leu Arg
    50                  55                  60

Thr Trp Leu Tyr Arg Ile Lys Pro Ser Val Thr His Glu Pro Phe Tyr
65                  70                  75                  80

Pro Arg Asn Pro Thr Asn Glu Arg Leu Val Gly Glu Phe Asp Arg Thr
                85                  90                  95

Thr Thr Val Ala Thr Pro Thr Gln Leu Arg Trp Arg Pro Ala Asp Val
            100                 105                 110

Pro Leu His Pro Gly Leu Asp Phe Ile Asp Gly Leu Tyr Thr Val Cys
        115                 120                 125

Gly Ala Gly Ser Ser Cys Leu Arg His Gly Tyr Ala Ile His Met Tyr
    130                 135                 140

Ala Ala Asn Lys Pro Met Asp Gly Cys Ser Leu Cys Asn Ala Asp Gly
145                 150                 155                 160

Asp Phe Leu Ile Val Pro Gln Gln Gly Arg Leu Phe Ile Thr Thr Glu
                165                 170                 175

Cys Gly Arg Leu Leu Val Ser Pro Gly Glu Ile Val Ile Pro Gln
            180                 185                 190

Gly Leu Arg Phe Ala Val Asp Leu Pro Asp Gly Pro Ser Arg Gly Tyr
        195                 200                 205

Val Ser Glu Ile Phe Gly Ala His Phe Gln Leu Pro Asp Leu Gly Pro
    210                 215                 220

Ile Gly Ala Asn Gly Leu Ala Ser Pro Arg Asp Phe Leu Ser Pro Thr
225                 230                 235                 240

Ala Trp Phe Glu Gln Glu His His Pro Gly Tyr Thr Ile Val His Lys
                245                 250                 255

Tyr Gly Gly Glu Leu Phe Ser Ala Thr Gln Asp Phe Ser Pro Phe Asn
            260                 265                 270

Val Val Ala Trp His Gly Asn Tyr Val Pro Tyr Lys Tyr Asp Leu Ser
        275                 280                 285

Lys Phe Cys Pro Phe Asn Thr Val Leu Leu Asp His Gly Asp Pro Ser
```

```
                 290                 295                 300
Val Asn Thr Val Leu Thr Ala Pro Thr Asp Lys Pro Gly Val Ala Leu
305                 310                 315                 320

Leu Asp Phe Val Ile Phe Pro Pro Arg Trp Leu Val Ala Glu Asn Thr
                325                 330                 335

Phe Arg Pro Pro Tyr Tyr His Arg Asn Cys Met Ser Glu Phe Met Gly
            340                 345                 350

Leu Ile Tyr Gly Ile Gly Ser Ser His Val Lys Arg Cys Lys Asp Asp
        355                 360                 365

Ala His Leu Gln Ala Lys Ala Asp Gly Phe Leu Pro Gly Gly Ala Ser
    370                 375                 380

Leu His Ser Cys Met Thr Pro His Gly Pro Asp Thr Lys Thr Tyr Glu
385                 390                 395                 400

Ala Thr Ile Ser Arg Ala Ala Ala Asn Glu Pro Ser Arg Leu Ser Gly
                405                 410                 415

Thr Leu Ala Phe Met Phe Glu Ser Trp Leu Ile Pro Arg Val Cys Pro
            420                 425                 430

Trp Ala Leu Asp Ser Pro Cys Arg Asp Leu Asp Tyr Tyr Gln Cys Trp
        435                 440                 445

Ile Gly Leu Lys Ser His Phe Ser Pro Pro Ala Ala Ala Val Asp Asp
    450                 455                 460

Glu Asn Glu
465

<210> SEQ ID NO 12
<211> LENGTH: 1994
<212> TYPE: DNA
<213> ORGANISM: Phaseolus vulgaris

<400> SEQUENCE: 12
ctttctttag tttcgtagaa gctcaactct tcactccacc ttcacttctc cactctatct     60
ttctctatgt tacttccgtc aatcatggac aacccaatcg ctgcccaaga tttcacctac    120
ctttccggct tcggaaacca cctctcctcc gaggctctcc ccggagcttt gccggagggg    180
cagaacagcc ctctcatctg ccccttcggt ctctacgccg agcaaatctc cggcacctcc    240
ttcacctccc ctcgcaaccg caaccgctgc agttggtttt accggatcaa accatcggtg    300
acccacgaac cgtttaaacc tagagtacct agtaactgga aattttcag tgagttcaac    360 agctccaaca gttctgctaa cccaactcag cttagatgga gcccatgga tgcacctgat    420 tcaccaacgg atttcattga tgggttgtcc accatttgtg ttctggaag ctctttcatg    480 cgccacggat atgctattca catgtacgct gcaaacaaat caatggacaa ttgtgccttt    540
tgcaatgctg atggtgactt cttgatagtt cccaacaag gaagactctt aatcaccact    600
gaatgtggaa ggttgaaagt ttccccgggt gaaattgcta tactacctca aggttttcgt    660
ttttctgtga atctgcctga tggtccttcg cgtggttatg ttgctgaaat atttggtact    720
cattttgaac ttcctgatct gggaccaata ggtgctaacg tcttgctgc ccaagggat    780 ttccttgttc ctactgcatg gtttgaagat aaatcctatc ctggctacac tatagtgcag    840
aagtttggtg gtgaactgtt tgccgcagtt caagatttct ctccctttaa tgttgttgct    900
tggcatggta attatttcc ataaagtat gatttaagca aattctgccc ttataatacg    960
gttctgtttg atcatagtga tccatcaatc aatactgtgc tgacagcacc aactgacaaa   1020
cctggagtgg cattacttga ttttgtcatt ttcccaccca gatggctggt tgctgagcac   1080
```

```
actttccggc tccatatta tcatcgcaac tgcatgagtg aatttatggg cctcattcat    1140
ggtggctatg aggccaaggc tgatggattt cttcctggtg gtgcaagtct ccataactgt    1200
atgactcccc atggtcccga taccaagtca tatgaggcta ccattgctcg aggtaatgat    1260
ataggacctt ccaagatcac agacacaatg gctttatgt ttgaatcaag tttaatacct    1320
cggatcagtc aatgggccct agaatcaccc ttcttggatc aagattatta ccagtgttgg    1380
attggcctga gatctcattt tacagttaaa accagagcat gcggaatgga cagtaaggag    1440
tgaaatgggt gcctcacagc tacaattgta tccctaataa cttacgatct tgtggtacat    1500
aaaaatagat gtaattataa aatataagag aaataatact tgtacaacaa attgtacaag    1560
gactaactag tctataatca gttggttggt tggttggttg ttgaacacga cacccaattg    1620
tgaattataa acattttgt ctacaaattt ttttaataaa agaatagatg ttgtagaata    1680
aagagaagag agaaaagatt gtaatgtaat aaatgatgaa atgaagagag aaagataaaa    1740
tattgtgaat tattgttgca tcatgtttta gaatatgatt cagtcggtta tgtacaataa    1800
aagctattgg agtattcaag ctcggttcgg ctaagagatg gaaaaatatg aaagagaaca    1860
acagtgtgaa agagagtgga tgtttaaatc tgattgaaga gttctgaaag ataaagaata    1920
taacagaaaa aaacgatatt gttcttacag tgtcgttaag tcatcagatg tggtgaattt    1980
gagatggtga atcc                                                     1994
```

<210> SEQ ID NO 13
<211> LENGTH: 458
<212> TYPE: PRT
<213> ORGANISM: Phaseolus vulgaris

<400> SEQUENCE: 13

```
Met Leu Leu Pro Ser Ile Met Asp Asn Pro Ile Ala Ala Gln Asp Phe
1               5                   10                  15

Thr Tyr Leu Ser Gly Phe Gly Asn His Leu Ser Ser Glu Ala Leu Pro
            20                  25                  30

Gly Ala Leu Pro Glu Gly Gln Asn Ser Pro Leu Ile Cys Pro Phe Gly
        35                  40                  45

Leu Tyr Ala Glu Gln Ile Ser Gly Thr Ser Phe Thr Ser Pro Arg Asn
    50                  55                  60

Arg Asn Arg Cys Ser Trp Phe Tyr Arg Ile Lys Pro Ser Val Thr His
65                  70                  75                  80

Glu Pro Phe Lys Pro Arg Val Pro Ser Asn Trp Lys Ile Phe Ser Glu
                85                  90                  95

Phe Asn Ser Ser Asn Ser Ala Asn Pro Thr Gln Leu Arg Trp Lys
            100                 105                 110

Pro Met Asp Ala Pro Asp Ser Pro Thr Asp Phe Ile Asp Gly Leu Ser
        115                 120                 125

Thr Ile Cys Gly Ser Gly Ser Ser Phe Met Arg His Gly Tyr Ala Ile
    130                 135                 140

His Met Tyr Ala Ala Asn Lys Ser Met Asp Asn Cys Ala Phe Cys Asn
145                 150                 155                 160

Ala Asp Gly Asp Phe Leu Ile Val Pro Gln Gln Gly Arg Leu Leu Ile
                165                 170                 175

Thr Thr Glu Cys Gly Arg Leu Lys Val Ser Pro Gly Glu Ile Ala Ile
            180                 185                 190

Leu Pro Gln Gly Phe Arg Phe Ser Val Asn Leu Pro Asp Gly Pro Ser
        195                 200                 205
```

```
Arg Gly Tyr Val Ala Glu Ile Phe Gly Thr His Phe Glu Leu Pro Asp
    210                 215                 220

Leu Gly Pro Ile Gly Ala Asn Gly Leu Ala Ala Pro Arg Asp Phe Leu
225                 230                 235                 240

Val Pro Thr Ala Trp Phe Glu Asp Lys Ser Tyr Pro Gly Tyr Thr Ile
                245                 250                 255

Val Gln Lys Phe Gly Gly Glu Leu Phe Ala Ala Val Gln Asp Phe Ser
            260                 265                 270

Pro Phe Asn Val Val Ala Trp His Gly Asn Tyr Phe Pro Tyr Lys Tyr
        275                 280                 285

Asp Leu Ser Lys Phe Cys Pro Tyr Asn Thr Val Leu Phe Asp His Ser
    290                 295                 300

Asp Pro Ser Ile Asn Thr Val Leu Thr Ala Pro Thr Asp Lys Pro Gly
305                 310                 315                 320

Val Ala Leu Leu Asp Phe Val Ile Phe Pro Pro Arg Trp Leu Val Ala
                325                 330                 335

Glu His Thr Phe Arg Pro Pro Tyr Tyr His Arg Asn Cys Met Ser Glu
            340                 345                 350

Phe Met Gly Leu Ile His Gly Gly Tyr Glu Ala Lys Ala Asp Gly Phe
        355                 360                 365

Leu Pro Gly Gly Ala Ser Leu His Asn Cys Met Thr Pro His Gly Pro
    370                 375                 380

Asp Thr Lys Ser Tyr Glu Ala Thr Ile Ala Arg Gly Asn Asp Ile Gly
385                 390                 395                 400

Pro Ser Lys Ile Thr Asp Thr Met Ala Phe Met Phe Glu Ser Ser Leu
                405                 410                 415

Ile Pro Arg Ile Ser Gln Trp Ala Leu Glu Ser Pro Phe Leu Asp Gln
            420                 425                 430

Asp Tyr Tyr Gln Cys Trp Ile Gly Leu Arg Ser His Phe Thr Val Lys
        435                 440                 445

Thr Arg Ala Cys Gly Met Asp Ser Lys Glu
    450                 455
```

<210> SEQ ID NO 14
<211> LENGTH: 1533
<212> TYPE: DNA
<213> ORGANISM: Ricinus communis

<400> SEQUENCE: 14

```
atggataacc ccaaaagcaa cggccgtgat tttccctccg acgatcatga ttacctatca     60
ggattcggca acaccttcga atcagaagcc attcatggag ctttaccacg tggacagaac    120
agccctctca tatgtcctta tggtctttat gctgaacaga tttctgggtc ttctttcact    180
tcccctcgca aactcagtca acgcagttgg ctatatcgaa ttaaaccatc tgttacacat    240
gaaccattta agccacgggt tccaagtcat ggaaagatag tcagtgaatt tgataaaaca    300
gatagttgta caacaacacc aactcagctt agatggaagc ctgttgatat tcctgattct    360
cccaccgatt ttattgatgg gttgttcact atttgtggtg ctggttcttc atttcttcgc    420
catggatttg ctattcacat gtacactgct aataagtcga tgggtaattg tgctctatgc    480
aatgctgatg gtgatttctt ggttgttccc caagaaggga ggttatggat cactactgaa    540
tgcggaaagc tgcaagtctc tcctggtgaa gtagttgttt tacctcaagg gtttcgtttt    600
gctgtagatt tgccagatgg tccatcacgt ggttatgttg ctgagatttt tggtacccat    660
tttcagcttc ctgatcttgg accaataggt gctaatggtc ttgctgctcc aagggatttc    720
```

-continued

```
cttgttccca aggcctggta tgaggagggt ccttgtccag gatacactat catacaaaag    780
tttggtggag aactatttac tgcaaaacag gatttctctc cttttaatgt agttgcctgg    840
catggtaatt ttgttccata taagtatgat ctcaaaaaat tttgccccta taatactgtt    900
ttgattgatc atagcgatcc atcaataaat acagttctga cagcttcaac tgataaacct    960
ggtgtggcat tgcttgattt tgtcatcttt cctcctcgat ggttggttgc tgagcatact   1020
ttccgacctc catattacca tcgtaattgt atgagtgaat ttatgggcct gatttatgga   1080
ggatatgagg caaaagctga tgggtttgtc ccaggtggtg cgagtcttca tagctgcatg   1140
actccacatg gtcctgatac caagacatat gaggctacca ttgcacgcgg gaatgatgca   1200
ggaccgagta gaatcactga tacaatggcc ttcatgtttg aatcatgttt gatccccagg   1260
atatgtctat gggctgttga gtccccattc atagaccatg attattacca gtgttggatt   1320
ggacttaaat cccatttttc tcatggagca gatagtaaga acggtggcat atagaatgaa   1380
tatcagggaa tctgcagtat tctgacataa gttgctttta cgacataatt cctgggcttg   1440
agatcccgct cagtatacct gtccagcatg tttatacata agaaaaataa gaagtagaaa   1500
tgcatataga agtaccaaat ataggaaaag cat                                1533

<210> SEQ ID NO 15
<211> LENGTH: 457
<212> TYPE: PRT
<213> ORGANISM: Ricinus communis
<400> SEQUENCE: 15

Met Asp Asn Pro Lys Ser Asn Gly Arg Asp Phe Pro Ser Asp Asp His
1               5                   10                  15

Asp Tyr Leu Ser Gly Phe Gly Asn Thr Phe Glu Ser Glu Ala Ile His
            20                  25                  30

Gly Ala Leu Pro Arg Gly Gln Asn Ser Pro Leu Ile Cys Pro Tyr Gly
        35                  40                  45

Leu Tyr Ala Glu Gln Ile Ser Gly Ser Ser Phe Thr Ser Pro Arg Lys
    50                  55                  60

Leu Ser Gln Arg Ser Trp Leu Tyr Arg Ile Lys Pro Ser Val Thr His
65                  70                  75                  80

Glu Pro Phe Lys Pro Arg Val Pro Ser His Gly Lys Ile Val Ser Glu
                85                  90                  95

Phe Asp Lys Thr Asp Ser Cys Thr Thr Thr Pro Thr Gln Leu Arg Trp
            100                 105                 110

Lys Pro Val Asp Ile Pro Asp Ser Pro Thr Asp Phe Ile Asp Gly Leu
        115                 120                 125

Phe Thr Ile Cys Gly Ala Gly Ser Ser Phe Leu Arg His Gly Phe Ala
    130                 135                 140

Ile His Met Tyr Thr Ala Asn Lys Ser Met Gly Asn Cys Ala Leu Cys
145                 150                 155                 160

Asn Ala Asp Gly Asp Phe Leu Val Val Pro Gln Glu Gly Arg Leu Trp
                165                 170                 175

Ile Thr Thr Glu Cys Gly Lys Leu Gln Val Ser Pro Gly Glu Val Val
            180                 185                 190

Val Leu Pro Gln Gly Phe Arg Phe Ala Val Asp Leu Pro Asp Gly Pro
        195                 200                 205

Ser Arg Gly Tyr Val Ala Glu Ile Phe Gly Thr His Phe Gln Leu Pro
    210                 215                 220
```

Asp Leu Gly Pro Ile Gly Ala Asn Gly Leu Ala Ala Pro Arg Asp Phe
225                 230                 235                 240

Leu Val Pro Lys Ala Trp Tyr Glu Glu Gly Pro Cys Pro Gly Tyr Thr
            245                 250                 255

Ile Ile Gln Lys Phe Gly Gly Glu Leu Phe Thr Ala Lys Gln Asp Phe
        260                 265                 270

Ser Pro Phe Asn Val Val Ala Trp His Gly Asn Phe Val Pro Tyr Lys
    275                 280                 285

Tyr Asp Leu Lys Lys Phe Cys Pro Tyr Asn Thr Val Leu Ile Asp His
290                 295                 300

Ser Asp Pro Ser Ile Asn Thr Val Leu Thr Ala Ser Thr Asp Lys Pro
305                 310                 315                 320

Gly Val Ala Leu Leu Asp Phe Val Ile Phe Pro Pro Arg Trp Leu Val
            325                 330                 335

Ala Glu His Thr Phe Arg Pro Pro Tyr Tyr His Arg Asn Cys Met Ser
        340                 345                 350

Glu Phe Met Gly Leu Ile Tyr Gly Gly Tyr Glu Ala Lys Ala Asp Gly
    355                 360                 365

Phe Val Pro Gly Ala Ser Leu His Ser Cys Met Thr Pro His Gly
370                 375                 380

Pro Asp Thr Lys Thr Tyr Glu Ala Thr Ile Ala Arg Gly Asn Asp Ala
385                 390                 395                 400

Gly Pro Ser Arg Ile Thr Asp Thr Met Ala Phe Met Phe Glu Ser Cys
            405                 410                 415

Leu Ile Pro Arg Ile Cys Leu Trp Ala Val Glu Ser Pro Phe Ile Asp
        420                 425                 430

His Asp Tyr Tyr Gln Cys Trp Ile Gly Leu Lys Ser His Phe Ser His
    435                 440                 445

Gly Ala Asp Ser Lys Asn Gly Gly Ile
450                 455

<210> SEQ ID NO 16
<211> LENGTH: 1386
<212> TYPE: DNA
<213> ORGANISM: Linum usitatissimum

<400> SEQUENCE: 16
atggaaacgc gacaggatca gctcctctca tcctcctcca cttgcggcgg cggcgatgag      60
ctcgattacc tctccgggtt cggcaacaac ttcgagtcag aggcgattgc tggagctctc     120
cctcgggatc agaacagccc gctagtatgc cctgcggtc tctatgcgga gcagatctca     180
gggacgtcgt ttacagctcc tcgcaagctc aatcaacgga gttggctcta taggatcaag     240
ccttcggtga cgcacgagcc gttccagcct cggatcccg ttcacgggaa gctggtgagc     300
gagttcaact gctccaacag cgtcaccacc ccgacgcagc tccgatggaa gcctgtggag     360
atccctgatt atcccactga ttttgtcgat ggattgttca ctgtctgcgg cgctggcagc     420
tccttcctcc gccatggatt tctattcac atgtatgctg ctaataaatc aatggagaat     480
tgtgccttct gcaatgctga tggtgacttc ttgcttgttc cgcaacacgg aaggttgtgg     540
ctcaccactg aatgtggaaa gttgcaagtt ctcctggtg aagttgccgt tctaccacaa     600
ggattcagat ttctgttga tgcctgat ggtccatcac gagggtacgt tgctgagata     660
tttggcaccc attttcagct tcccgatctt gggccaatag gtgccaatgg tcttgctgct     720
tcaagggatt tccttgttcc caaggcctgg tatgaagagg acatgcgtcc aggatataca     780

```
attgtgcaga agtttggagg agaactttc accgcaaaac aagattttc accctttcaat    840
gtagttgctt ggcatggtaa ctacgtacca tacaagtatg atctgagtaa gttttgccct    900
tacaacacag ttttggttga tcatagtgat ccatcaataa acacagtact gacggctcca    960
actgacaaac ctggagtggc gttgcttgat tttgtgatat ttcctccacg atggctagtt   1020
gcggagcata catttcggcc tccatattac catcgtaact gcatgagtga atttatgggg   1080
ttgatttctg gtggatacga ggcgaaggct gatgggtttc tgccaggtgg tgcaagcctt   1140
cacagctgca tgacgcccca cggccctgat accaaaactt acgagactac tatcgccctt   1200
gggaatgatg caaaaccaca taaaatcacc aatacaatgg ctttcatgtt tgagtcatgc   1260
ctcatcccga gaatctgcct atgggcactc gactcaacct ctagggatca tgattattac   1320
caatgttgga ttggactgaa atcccacttc aatgtcgagg aagcaataca gaatggagga   1380
acttga                                                              1386
```

<210> SEQ ID NO 17
<211> LENGTH: 461
<212> TYPE: PRT
<213> ORGANISM: Linum usitatissimum

<400> SEQUENCE: 17

```
Met Glu Thr Arg Gln Asp Gln Leu Leu Ser Ser Ser Thr Cys Gly
1               5                   10                  15

Gly Gly Asp Glu Leu Asp Tyr Leu Ser Gly Phe Gly Asn Asn Phe Glu
            20                  25                  30

Ser Glu Ala Ile Ala Gly Ala Leu Pro Arg Asp Gln Asn Ser Pro Leu
        35                  40                  45

Val Cys Pro Cys Gly Leu Tyr Ala Glu Gln Ile Ser Gly Thr Ser Phe
    50                  55                  60

Thr Ala Pro Arg Lys Leu Asn Gln Arg Ser Trp Leu Tyr Arg Ile Lys
65                  70                  75                  80

Pro Ser Val Thr His Glu Pro Phe Gln Pro Arg Ile Pro Val His Gly
                85                  90                  95

Lys Leu Val Ser Glu Phe Asn Cys Ser Asn Ser Val Thr Thr Pro Thr
            100                 105                 110

Gln Leu Arg Trp Lys Pro Val Glu Ile Pro Asp Tyr Pro Thr Asp Phe
        115                 120                 125

Val Asp Gly Leu Phe Thr Val Cys Gly Ala Gly Ser Ser Phe Leu Arg
    130                 135                 140

His Gly Phe Ser Ile His Met Tyr Ala Ala Asn Lys Ser Met Glu Asn
145                 150                 155                 160

Cys Ala Phe Cys Asn Ala Asp Gly Asp Phe Leu Leu Val Pro Gln His
                165                 170                 175

Gly Arg Leu Trp Leu Thr Thr Glu Cys Gly Lys Leu Gln Val Ser Pro
            180                 185                 190

Gly Glu Val Ala Val Leu Pro Gln Gly Phe Arg Phe Ser Val Glu Met
        195                 200                 205

Pro Asp Gly Pro Ser Arg Gly Tyr Val Ala Glu Ile Phe Gly Thr His
    210                 215                 220

Phe Gln Leu Pro Asp Leu Gly Pro Ile Gly Ala Asn Gly Leu Ala Ala
225                 230                 235                 240

Ser Arg Asp Phe Leu Val Pro Lys Ala Trp Tyr Glu Glu Asp Met Arg
                245                 250                 255

Pro Gly Tyr Thr Ile Val Gln Lys Phe Gly Gly Glu Leu Phe Thr Ala
```

```
            260             265             270
Lys Gln Asp Phe Ser Pro Phe Asn Val Val Ala Trp His Gly Asn Tyr
        275                 280                 285

Val Pro Tyr Lys Tyr Asp Leu Ser Lys Phe Cys Pro Tyr Asn Thr Val
        290                 295                 300

Leu Val Asp His Ser Asp Pro Ser Ile Asn Thr Val Leu Thr Ala Pro
305                 310                 315                 320

Thr Asp Lys Pro Gly Val Ala Leu Leu Asp Phe Val Ile Phe Pro Pro
                325                 330                 335

Arg Trp Leu Val Ala Glu His Thr Phe Arg Pro Pro Tyr Tyr His Arg
            340                 345                 350

Asn Cys Met Ser Glu Phe Met Gly Leu Ile Ser Gly Gly Tyr Glu Ala
        355                 360                 365

Lys Ala Asp Gly Phe Leu Pro Gly Gly Ala Ser Leu His Ser Cys Met
        370                 375                 380

Thr Pro His Gly Pro Asp Thr Lys Thr Tyr Glu Thr Thr Ile Ala Leu
385                 390                 395                 400

Gly Asn Asp Ala Lys Pro His Lys Ile Thr Asn Thr Met Ala Phe Met
                405                 410                 415

Phe Glu Ser Cys Leu Ile Pro Arg Ile Cys Leu Trp Ala Leu Asp Ser
            420                 425                 430

Thr Ser Arg Asp His Asp Tyr Tyr Gln Cys Trp Ile Gly Leu Lys Ser
        435                 440                 445

His Phe Asn Val Glu Glu Ala Ile Gln Asn Gly Gly Thr
450                 455                 460

<210> SEQ ID NO 18
<211> LENGTH: 1845
<212> TYPE: DNA
<213> ORGANISM: Populus balsamifera subsp. trichocarpa

<400> SEQUENCE: 18
cgaatagatt atgatgccac gtcaatatca tccaccccat cctcttctct gcaagagaca      60
agagctataa aattaattcc gttgatggcc tcactcttcc ccacaaatca attgaagaga     120
tattccaatg gagcaggagc agcagcagat caccataacc aatgatttcc cctccgacga     180
tcatgattat ctatcgggat cggcaacac cttcgaatcc gaatccatcc ctggatcatt      240
gcctcgcaga cagaacagcc ctctcttatg ccctacggt ctctacgcag aacagatctc      300
cggcacctcc ttcacttccc ctcacaaact caaccaacgc agttggttat atagaatcaa     360
gccatcggtc actcacgagc cgtttcaggc aaggtttcca aggcacgata aactcgtgag     420
tgaatttgat aaatcaaaca gttatacaac gcccacgcaa ctgcggtgga agccaaagcc     480
agtagatact gttgaagaat cagcaccaat tgattttgtt gagggcttgt atacagtttg     540
tggagctggc agctccttcc tccgccatgg atttgctatt cacatgtata ccgccaataa     600
atccatggat gatcgtgctt tttgcaatgc cgatggcgat tcttgattg ttccacaaaa      660 aggaagattg tggatcgcta ctgaatgtgg gaaattgcaa gtctctcctg gtgaaattgt     720
tgttatacct caaggattcc gtttcgctgt agatttgcca gatggcccgt cacgtggtta     780
tgtgtctgag atttttggaa cccatttca acttcctgat cttgggccaa taggtgctaa      840
tggtcttgct gctccaaggg atttccttgt tcccaaggcc tggtttgaag atggttccag     900
accaggatac actgtcgttc aaaagtatgg tggagaactt tttgttgcaa acaagatttt     960
ttctcccttc aatgtggttg cttggcatgg taattatgtt ccatataagt atgatctcaa    1020
```

-continued

```
taagttttgc ccttataata ctgtcttgtt tgatcacagt gatccatcaa taaatacagt    1080
tttgactgca ccaactgata aacctggcgt ggcattgctt gattttgtta ttttttcctcc   1140 ccgatggctg gttgctgagc atacgttccg acctccatac taccatcgca attgtatgag    1200
tgaatttatg ggcctgattt atggtggata tgaggcaaaa gctgacggct ttctcccagg    1260
aggtgcaagc cttcatagct gcatgactcc acatggtcct gatacaaaga catacgaggc    1320
taccattgag agtgggcatg atgcaggacc atccaaaatc actaatacac tggctttcat    1380
gtttgaatca tgtttaattc ccaggatcag cctttgtgct cttaagtcac cgttaatgga    1440
taatgattac taccaatgct ggactggact caaatcccat ttttccggcg aaggagcaga    1500
tagcaaaggc aatggtgtat agaattcacc caagggaacc cgaagcggag gtaactcaga    1560
tctgatttgg tctttaatat aaaccttggg catgcatgag cctttattcg gtgaaacttg    1620
acagcttagt tttgtacata taaagaagg tgaatatata aatagaaata gaaataatca     1680
aatacaggaa atgtagcctt ttatcttatg tgatcaacac taatcaatga atgcatttg     1740 tacataacgt gtgcacattg ttgtctggct gggatacttg ttacttttca ctgagccaat    1800
caaaaagttg gaggataatg ccatgaacag ctaagacgca cttgt                    1845
```

<210> SEQ ID NO 19
<211> LENGTH: 464
<212> TYPE: PRT
<213> ORGANISM: Populus balsamifera subsp. trichocarpa

<400> SEQUENCE: 19

```
Met Glu Gln Glu Gln Gln Gln Ile Thr Ile Thr Asn Asp Phe Pro Ser
1               5                   10                  15

Asp Asp His Asp Tyr Leu Ser Gly Phe Gly Asn Thr Phe Glu Ser Glu
            20                  25                  30

Ser Ile Pro Gly Ser Leu Pro Arg Arg Gln Asn Ser Pro Leu Leu Cys
        35                  40                  45

Pro Tyr Gly Leu Tyr Ala Glu Gln Ile Ser Gly Thr Ser Phe Thr Ser
    50                  55                  60

Pro His Lys Leu Asn Gln Arg Ser Trp Leu Tyr Arg Ile Lys Pro Ser
65                  70                  75                  80

Val Thr His Glu Pro Phe Gln Ala Arg Phe Pro Arg His Asp Lys Leu
                85                  90                  95

Val Ser Glu Phe Asp Lys Ser Asn Ser Tyr Thr Thr Pro Thr Gln Leu
            100                 105                 110

Arg Trp Lys Pro Lys Pro Val Asp Thr Val Glu Glu Ser Ala Pro Ile
        115                 120                 125

Asp Phe Val Glu Gly Leu Tyr Thr Val Cys Gly Ala Gly Ser Ser Phe
    130                 135                 140

Leu Arg His Gly Phe Ala Ile His Met Tyr Thr Ala Asn Lys Ser Met
145                 150                 155                 160

Asp Asp Arg Ala Phe Cys Asn Ala Asp Gly Asp Phe Leu Ile Val Pro
                165                 170                 175

Gln Lys Gly Arg Leu Trp Ile Ala Thr Glu Cys Gly Lys Leu Gln Val
            180                 185                 190

Ser Pro Gly Glu Ile Val Val Ile Pro Gln Gly Phe Arg Phe Ala Val
        195                 200                 205

Asp Leu Pro Asp Gly Pro Ser Arg Gly Tyr Val Ser Glu Ile Phe Gly
    210                 215                 220
```

Thr His Phe Gln Leu Pro Asp Leu Gly Pro Ile Gly Ala Asn Gly Leu
225                 230                 235                 240

Ala Ala Pro Arg Asp Phe Leu Val Pro Lys Ala Trp Phe Glu Asp Gly
            245                 250                 255

Ser Arg Pro Gly Tyr Thr Val Val Gln Lys Tyr Gly Gly Glu Leu Phe
        260                 265                 270

Val Ala Lys Gln Asp Phe Ser Pro Phe Asn Val Val Ala Trp His Gly
    275                 280                 285

Asn Tyr Val Pro Tyr Lys Tyr Asp Leu Asn Lys Phe Cys Pro Tyr Asn
290                 295                 300

Thr Val Leu Phe Asp His Ser Asp Pro Ser Ile Asn Thr Val Leu Thr
305                 310                 315                 320

Ala Pro Thr Asp Lys Pro Gly Val Ala Leu Leu Asp Phe Val Ile Phe
            325                 330                 335

Pro Pro Arg Trp Leu Val Ala Glu His Thr Phe Arg Pro Pro Tyr Tyr
        340                 345                 350

His Arg Asn Cys Met Ser Glu Phe Met Gly Leu Ile Tyr Gly Gly Tyr
    355                 360                 365

Glu Ala Lys Ala Asp Gly Phe Leu Pro Gly Gly Ala Ser Leu His Ser
370                 375                 380

Cys Met Thr Pro His Gly Pro Asp Thr Lys Thr Tyr Glu Ala Thr Ile
385                 390                 395                 400

Glu Ser Gly His Asp Ala Gly Pro Ser Lys Ile Thr Asn Thr Leu Ala
            405                 410                 415

Phe Met Phe Glu Ser Cys Leu Ile Pro Arg Ile Ser Leu Cys Ala Leu
        420                 425                 430

Lys Ser Pro Leu Met Asp Asn Asp Tyr Tyr Gln Cys Trp Thr Gly Leu
    435                 440                 445

Lys Ser His Phe Ser Gly Glu Gly Ala Asp Ser Lys Gly Asn Gly Val
450                 455                 460

<210> SEQ ID NO 20
<211> LENGTH: 1816
<212> TYPE: DNA
<213> ORGANISM: Sorghum bicolor

<400> SEQUENCE: 20
aacatgcact gccgtgccgt ctccgagtag agtaggctgc tctgctctgc tctgcttgct     60
gacgtgctgt tggcctgagc ctgggcgtcg tcgccatcgg caatggccat ggaggagcag    120
cagccaccct ctgctcctgc tcctgcgccg ccggagctgc gctacctctc ggggctgggc    180
aacagcttct cgtcggaggc ggtgccgggg tcgctccccg tggggcagaa cagcccgctg    240
gtgtgcccgc tgggactcta cgccgagcag ctctccggca cctccttcac caccccgcgc    300
gcccggaacc tccgcacgtg gctgtaccgg atcaagccat cggtgaccca cgagcccttc    360
tacccgcgga accccaccaa cgagcgcctc gtcggcgagt ccaccgggc accaccgtc    420 gccacgccca cgcagctgcg ctggagaccc gccgacgtgc ccctccaccc ggacctcgac    480
ttcatcgacg gctctacac cgtctgcggc gccggcagct cttgcctccg acacggatac    540
gccatccaca tgtatgctgc taacaagtcc atggatggat gcgccttctg caatgccgac    600
ggtgacttcc tcattgttcc ccagcaagga aggctattga tcacaactga gtgcggaaag    660
ctgctcgttt cacccggcga gatcgtcgtg attcctcaag gtttccgctt gctgttgac    720 ttgccggatg gcccctcgcg tggctatgtc tctgagatct tcggcaccca ttttcagctc    780

```
cctgatcttg gcccaattgg tgctaatggt ttggcttcac cgagggattt cctttccccg    840
acagcatggt ttgagcagga ccaccaccct ggatacacaa tagtgcagaa gtatggcggt    900
gagctgttca ctgccacgca ggattttct ccattcaatg tggtcgcatg catgggaat    960
tatgtccctt acaagtatga tctgagtaag ttctgtccat tcaacaccgt cctctttgac   1020
catggcgacc catcggtaaa cacagttcta actgcgccaa ctgataagcc tggcgtcgcg   1080
ttgcttgatt ttgtaatatt cccacctaga tggctggttg ctgaaaatac attccggcct   1140
ccgtactacc accgcaactg catgagcgaa ttcatgggcc tcatttatgg gatatatgag   1200
gctaaggccg atggttttct tcctggaggt gccagtcttc acagctgcat gacaccacat   1260
gggccagaca ccaagacata tgaggcaaca atcagccgtg ctggtgccaa cgagccattc   1320
aggctcagtg aacgttggc cttcatgttt gagtcttcgc ttatccctcg cgtgtgtcga   1380
tgggctctgg attccccgtg tcgagatctc gattactacc agtgctggat tggattgaag   1440
tcccactttt cacatgacaa cggtggagtg gcgaccatcg agcctgctgc tggcacggat   1500
gagaaagagt agctagctgg cttactgcag cagcctccga tcctcgcttc gcttgtgtat   1560
actactatgt gctccgctag tttataagct gtgttgtgta caagtacaag gtagaataaa   1620
tcttcgtcga acgagagagg cacaaggaaa catacattac aaactctgct cagctggctc   1680
ttgtcttggg tactcagctg taatgctagc tctgcagtct gtagaatgta ctactgtcac   1740
cagtgtgcat atccataacg tacagaagca agcaatttgc agcaatagca tgggaataaa   1800
tgacagatta cataca                                                    1816
```

<210> SEQ ID NO 21
<211> LENGTH: 469
<212> TYPE: PRT
<213> ORGANISM: Sorghum bicolor

<400> SEQUENCE: 21

```
Met Ala Met Glu Glu Gln Gln Pro Pro Ala Pro Ala Pro Ala Pro
1               5                   10                  15

Pro Glu Leu Arg Tyr Leu Ser Gly Leu Gly Asn Ser Phe Ser Ser Glu
            20                  25                  30

Ala Val Pro Gly Ser Leu Pro Val Gly Gln Asn Ser Pro Leu Val Cys
        35                  40                  45

Pro Leu Gly Leu Tyr Ala Glu Gln Leu Ser Gly Thr Ser Phe Thr Thr
    50                  55                  60

Pro Arg Ala Arg Asn Leu Arg Thr Trp Leu Tyr Arg Ile Lys Pro Ser
65                  70                  75                  80

Val Thr His Glu Pro Phe Tyr Pro Arg Asn Pro Thr Asn Glu Arg Leu
                85                  90                  95

Val Gly Glu Phe His Arg Ala Thr Thr Val Ala Thr Pro Thr Gln Leu
            100                 105                 110

Arg Trp Arg Pro Ala Asp Val Pro Leu His Pro Asp Leu Asp Phe Ile
        115                 120                 125

Asp Gly Leu Tyr Thr Val Cys Gly Ala Gly Ser Ser Cys Leu Arg His
    130                 135                 140

Gly Tyr Ala Ile His Met Tyr Ala Ala Asn Lys Ser Met Asp Gly Cys
145                 150                 155                 160

Ala Phe Cys Asn Ala Asp Gly Asp Phe Leu Ile Val Pro Gln Gln Gly
                165                 170                 175

Arg Leu Leu Ile Thr Thr Glu Cys Gly Lys Leu Leu Val Ser Pro Gly
            180                 185                 190
```

Glu Ile Val Val Ile Pro Gln Gly Phe Arg Phe Ala Val Asp Leu Pro
    195                 200                 205

Asp Gly Pro Ser Arg Gly Tyr Val Ser Glu Ile Phe Gly Thr His Phe
    210                 215                 220

Gln Leu Pro Asp Leu Gly Pro Ile Gly Ala Asn Gly Leu Ala Ser Pro
225                 230                 235                 240

Arg Asp Phe Leu Ser Pro Thr Ala Trp Phe Glu Gln Asp His His Pro
                245                 250                 255

Gly Tyr Thr Ile Val Gln Lys Tyr Gly Gly Glu Leu Phe Thr Ala Thr
                260                 265                 270

Gln Asp Phe Ser Pro Phe Asn Val Ala Trp His Gly Asn Tyr Val
                275                 280                 285

Pro Tyr Lys Tyr Asp Leu Ser Lys Phe Cys Pro Phe Asn Thr Val Leu
                290                 295                 300

Phe Asp His Gly Asp Pro Ser Val Asn Thr Val Leu Thr Ala Pro Thr
305                 310                 315                 320

Asp Lys Pro Gly Val Ala Leu Leu Asp Phe Val Ile Phe Pro Pro Arg
                325                 330                 335

Trp Leu Val Ala Glu Asn Thr Phe Arg Pro Pro Tyr Tyr His Arg Asn
                340                 345                 350

Cys Met Ser Glu Phe Met Gly Leu Ile Tyr Gly Ile Tyr Glu Ala Lys
                355                 360                 365

Ala Asp Gly Phe Leu Pro Gly Gly Ala Ser Leu His Ser Cys Met Thr
370                 375                 380

Pro His Gly Pro Asp Thr Lys Thr Tyr Glu Ala Thr Ile Ser Arg Ala
385                 390                 395                 400

Gly Ala Asn Glu Pro Phe Arg Leu Ser Gly Thr Leu Ala Phe Met Phe
                405                 410                 415

Glu Ser Ser Leu Ile Pro Arg Val Cys Arg Trp Ala Leu Asp Ser Pro
                420                 425                 430

Cys Arg Asp Leu Asp Tyr Tyr Gln Cys Trp Ile Gly Leu Lys Ser His
                435                 440                 445

Phe Ser His Asp Asn Gly Val Ala Thr Ile Glu Pro Ala Ala Gly
    450                 455                 460

Thr Asp Glu Lys Glu
465

<210> SEQ ID NO 22
<211> LENGTH: 1792
<212> TYPE: DNA
<213> ORGANISM: Panicum virgatum

<400> SEQUENCE: 22
ggcagttgca gcagccagca cagacagcag tcagcaggac aggagccttg ccccgctcgt    60
ctcctcctcc gcaatctgcc atggccgcgc aggaggagga gcagctgcgc tacctctccg   120
gactgggcaa caccttctcg tcggaggcgg tgccggggtc gctccccgtc ggccagaaca   180
gcccgctggt gtgcccgcgg ggcctctacg ccgagcagct ctccggcacc tccttcacca   240
ccccacgggc ccagaacctg cgcacgtggc tgtaccggat caagccatcg gtgacccacg   300
agcccttcca ccccgcccca gccgcccacg ccgcctcgt cggggagttc gaccgctcca   360
cagccgccgc cacgcccacg cagctgcgct ggaggccgcc cgaggtgccc ctggaccccg   420
ccctcgactt catcgacggc ctctacaccg tctgcggcgc cgggagctcc ttcctccgac   480

```
atggatacgc catccacatg tacgctgcta acaagtccat ggacggatgc gccttctgca      540
atgcggatgg tgatttcctc attgttcccc agcaaggaag gttgttgatc acaaccgaat      600
gtggaaaggt gctagtttca cctggcgaaa ttgttgtgat cctcaaggc ttccgctttg       660
ccattgactt gcctgatggc ccctcacgtg ctacgcttc tgagattttc ggcacccact       720
ttcagctccc tgatcttggc ccaatcggtg ccaatggttt ggcttcacca agggatttcc      780
tttcccccac agcatggttt gagcaggtcc accgccctgg gtacacaata gtgcacaagt      840
acggtggtga actattcact gccacgcagg atttttctcc gttcaatgtg gttgcatggc      900
atgggaatta tgtcccatat aagtatgatt tgagtaggtt ctgcccattt aatacggtcc      960
tatttgatca tggtgaccct tcagtaaaca cagtccttac tgcgccaact gataagcctg     1020
gtgtcgcatt acttgatttt gtaatattcc cacctaggtg gttggttgct gaaaatacat     1080
tccgccctcc atactaccat cgcaactgca tgagtgagtt catgggcctg atttatggga     1140
tatacgaggc taaggctgat ggttttctcc ccggaggtgc tagcctgcac agctgcatga     1200
caccacatgg accagacacc aagacatacg aggcaacgat cagccgtgct gatgccaatg     1260
agccattcag gctcagtggt acgctggcgt tcatgttcga gtcttcgctc atccctcgtg     1320
tgtgccggtg ggctcttgat tcgccgtatc gagatcttga ttactaccaa tgttggattg     1380
gattgaagtc ccacttctca catgacagtg gagccacagc cagcgagcct gctgcaagtc     1440
catagccgtc gtgttgtgta aaagcaaggc agaataatag agaccccagc tagggggtg      1500
gtcataatct gtatgtaata ataagctgca gtctgtagta tagaatataa cagatgcaag     1560
caagcaagca gttagcatct gcgggtagat agattgcaca tatgaaggat ccgatgtttt     1620
atgtctgaaa caagcaagca agcattggct ggctcctgag gtgttttaat ttgtggtgcc     1680
atgttgatcg agaaaagggg gttccgaggc aacgtagagt gcgacttgca ttgtgagagg     1740
aaaagttgtg gcatggatgg aatatatgtg atattttagc tgtcggtttc ac             1792
```

<210> SEQ ID NO 23
<211> LENGTH: 454
<212> TYPE: PRT
<213> ORGANISM: Panicum virgatum

<400> SEQUENCE: 23

```
Met Ala Ala Gln Glu Glu Glu Gln Leu Arg Tyr Leu Ser Gly Leu Gly
1               5                   10                  15

Asn Thr Phe Ser Ser Glu Ala Val Pro Gly Ser Leu Pro Val Gly Gln
            20                  25                  30

Asn Ser Pro Leu Val Cys Pro Arg Gly Leu Tyr Ala Glu Gln Leu Ser
        35                  40                  45

Gly Thr Ser Phe Thr Thr Pro Arg Ala Gln Asn Leu Arg Thr Trp Leu
    50                  55                  60

Tyr Arg Ile Lys Pro Ser Val Thr His Glu Pro Phe His Pro Arg Pro
65                  70                  75                  80

Ala Ala His Gly Arg Leu Val Gly Glu Phe Asp Arg Ser Thr Ala Ala
                85                  90                  95

Ala Thr Pro Thr Gln Leu Arg Trp Arg Pro Glu Val Pro Leu Asp
            100                 105                 110

Pro Pro Leu Asp Phe Ile Asp Gly Leu Tyr Thr Val Cys Gly Ala Gly
        115                 120                 125

Ser Ser Phe Leu Arg His Gly Tyr Ala Ile His Met Tyr Ala Ala Asn
    130                 135                 140
```

```
Lys Ser Met Asp Gly Cys Ala Phe Cys Asn Ala Asp Gly Asp Phe Leu
145                 150                 155                 160

Ile Val Pro Gln Gln Gly Arg Leu Leu Ile Thr Thr Glu Cys Gly Lys
            165                 170                 175

Val Leu Val Ser Pro Gly Glu Ile Val Val Ile Pro Gln Gly Phe Arg
        180                 185                 190

Phe Ala Ile Asp Leu Pro Asp Gly Pro Ser Arg Gly Tyr Ala Ser Glu
    195                 200                 205

Ile Phe Gly Thr His Phe Gln Leu Pro Asp Leu Gly Pro Ile Gly Ala
210                 215                 220

Asn Gly Leu Ala Ser Pro Arg Asp Phe Leu Ser Pro Thr Ala Trp Phe
225                 230                 235                 240

Glu Gln Val His Arg Pro Gly Tyr Thr Ile Val His Lys Tyr Gly Gly
            245                 250                 255

Glu Leu Phe Thr Ala Thr Gln Asp Phe Ser Pro Phe Asn Val Val Ala
        260                 265                 270

Trp His Gly Asn Tyr Val Pro Tyr Lys Tyr Asp Leu Ser Arg Phe Cys
    275                 280                 285

Pro Phe Asn Thr Val Leu Phe Asp His Gly Asp Pro Ser Val Asn Thr
290                 295                 300

Val Leu Thr Ala Pro Thr Asp Lys Pro Gly Val Ala Leu Leu Asp Phe
305                 310                 315                 320

Val Ile Phe Pro Pro Arg Trp Leu Val Ala Glu Asn Thr Phe Arg Pro
            325                 330                 335

Pro Tyr Tyr His Arg Asn Cys Met Ser Glu Phe Met Gly Leu Ile Tyr
        340                 345                 350

Gly Ile Tyr Glu Ala Lys Ala Asp Gly Phe Leu Pro Gly Gly Ala Ser
    355                 360                 365

Leu His Ser Cys Met Thr Pro His Gly Pro Asp Thr Lys Thr Tyr Glu
370                 375                 380

Ala Thr Ile Ser Arg Ala Asp Ala Asn Glu Pro Phe Arg Leu Ser Gly
385                 390                 395                 400

Thr Leu Ala Phe Met Phe Glu Ser Ser Leu Ile Pro Arg Val Cys Arg
            405                 410                 415

Trp Ala Leu Asp Ser Pro Tyr Arg Asp Leu Asp Tyr Tyr Gln Cys Trp
        420                 425                 430

Ile Gly Leu Lys Ser His Phe Ser His Asp Ser Gly Ala Thr Ala Ser
    435                 440                 445

Glu Pro Ala Ala Ser Pro
    450

<210> SEQ ID NO 24
<211> LENGTH: 1214
<212> TYPE: DNA
<213> ORGANISM: Manihot esculenta

<400> SEQUENCE: 24
ttctgtttgt aggtacgcag ctaacaaatc gatggaaaac tgtgctttct gcaatgctga    60
tggtgacttc ttgatagttc cccagcaagg aaggttatgg atcactactg aatgggaaa    120 gctgcaagtc tctccgggtg aaattgttgt tttacctcaa ggattccgtt ttgctgtaga   180
ttttccggat ggtccatcac gtggttatgt tgctgagatt tatggtaccc atttccagct   240
tcctgatctt gggccaatag gtgctaatgg tcttgctgct tcaagggatt tcttgttcc   300 taaggcctgg tttgaggagt gttctcgtcc aggatacact atcatacaaa agtttggtgg   360
```

```
agaactattt actgcaaaac aggattttc tcctttcaat gtagttgcct ggcatggtaa      420
ttatgttcca tataaatatg atctcaaaaa gttttgcccc tataatactg tgttgattga      480
tcatagtgat ccatcaataa atacagttct gacagcacca actgataagc ctggagtggc      540
gttgattgac tttgttgttt ttcctcctcg gtggttggtt gctgagcata ctttcagacc      600
tccgtattac catcgcaatt gtatgagtga atttatgggc ctgatttatg gtggatatga      660
ggcaaaagcc gatggattcc tcccaggtgg tgcaagtctt catagctgca tgactccaca      720
tggtcctgat acaaagacat atgaggctac cattgcacag gggaatgatg caggaccgta      780
taaaatcacc aatacaatgg ctttcatgtt tgaatcagct ttaatcccca gaatctgcaa      840
atgggcagtt gagtccccat ctgtggatca tgattattac cagtgttgga ttggactcaa      900
atcccatttt tcacatggag cagatgctaa cagcaatggc gtataaaatg gacgccatgg      960
tcatggaact tgaatgtatt gtggctcaaa tgtgatcatc aaacagaaat actgggcgtg     1020
agctttcctt ctgctcaatt gttcactgtg cagcatgtat atacagaaag gaataattga     1080
aaggaacata aattatattg aactatagaa attgttgttt ttctgtgttc tgcatggcca     1140
gcgttcagca gtgctgctat gacttgggat tattgtttgt taaggttatg aatggttaaa     1200
cttaaatatt tagc                                                       1214
```

<210> SEQ ID NO 25
<211> LENGTH: 304
<212> TYPE: PRT
<213> ORGANISM: Manihot esculenta

<400> SEQUENCE: 25

```
Met Glu Asn Cys Ala Phe Cys Asn Ala Asp Gly Asp Phe Leu Ile Val
1               5                   10                  15

Pro Gln Gln Gly Arg Leu Trp Ile Thr Thr Glu Cys Gly Lys Leu Gln
            20                  25                  30

Val Ser Pro Gly Glu Ile Val Val Leu Pro Gln Gly Phe Arg Phe Ala
        35                  40                  45

Val Asp Phe Pro Asp Gly Pro Ser Arg Gly Tyr Val Ala Glu Ile Tyr
    50                  55                  60

Gly Thr His Phe Gln Leu Pro Asp Leu Gly Pro Ile Gly Ala Asn Gly
65                  70                  75                  80

Leu Ala Ala Ser Arg Asp Phe Leu Val Pro Lys Ala Trp Phe Glu Glu
                85                  90                  95

Cys Ser Arg Pro Gly Tyr Thr Ile Ile Gln Lys Phe Gly Gly Glu Leu
            100                 105                 110

Phe Thr Ala Lys Gln Asp Phe Ser Pro Phe Asn Val Val Ala Trp His
        115                 120                 125

Gly Asn Tyr Val Pro Tyr Lys Tyr Asp Leu Lys Lys Phe Cys Pro Tyr
    130                 135                 140

Asn Thr Val Leu Ile Asp His Ser Asp Pro Ser Ile Asn Thr Val Leu
145                 150                 155                 160

Thr Ala Pro Thr Asp Lys Pro Gly Val Ala Leu Ile Asp Phe Val Val
                165                 170                 175

Phe Pro Pro Arg Trp Leu Val Ala Glu His Thr Phe Arg Pro Pro Tyr
            180                 185                 190

Tyr His Arg Asn Cys Met Ser Glu Phe Met Gly Leu Ile Tyr Gly Gly
        195                 200                 205

Tyr Glu Ala Lys Ala Asp Gly Phe Leu Pro Gly Gly Ala Ser Leu His
```

|  | 210 | | | 215 | | | | 220 | | | |
|---|---|---|---|---|---|---|---|---|---|---|---|

Ser Cys Met Thr Pro His Gly Pro Asp Thr Lys Thr Tyr Glu Ala Thr
225                 230                 235                 240

Ile Ala Gln Gly Asn Asp Ala Gly Pro Tyr Lys Ile Thr Asn Thr Met
                245                 250                 255

Ala Phe Met Phe Glu Ser Ala Leu Ile Pro Arg Ile Cys Lys Trp Ala
            260                 265                 270

Val Glu Ser Pro Ser Val Asp His Asp Tyr Tyr Gln Cys Trp Ile Gly
        275                 280                 285

Leu Lys Ser His Phe Ser His Gly Ala Asp Ala Asn Ser Asn Gly Val
    290                 295                 300

<210> SEQ ID NO 26
<211> LENGTH: 1620
<212> TYPE: DNA
<213> ORGANISM: Lycopersicon esculentum

<400> SEQUENCE: 26

| cacgagagaa cttccaattt tccttctgat ttggagtacc aaacaggatt tgggaatcat | 60 |
|---|---|
| ttttcatctg aagctatagt tggagctcta cctcaaggtc aaaatagtcc tcttatttgc | 120 |
| cccttttggac tttatgctga gcagatctct ggcacctctt ttacttcccc tcgcaaactt | 180 |
| aatcaacgca gttggctata tcgtattaag ccatcggtta cacatgaacc gtttagacca | 240 |
| agaatgccga gacatgaaaa gcttgtgagt gaattcaacc agtcaaacag ttctgctaca | 300 |
| ccaactcaac taaggtggaa gcctgttgag ataccagaaa caccgactga tttcattgat | 360 |
| ggtttgtata ctatatgcgg ggctggcagc tcatatctcc gacatggttt tgcaattcac | 420 |
| atgtatactg ccaacaaatc aatggagaac tctgccttct gcaatgctga tggcgacttt | 480 |
| ctgattgttc ctcaaaaagg aaggctgtgg attactactg aatgcggaag attgcaggtt | 540 |
| tgtcctggtg aaattgtgat tttgcctcaa ggatataggt tgctgttga ccttccggat | 600 |
| ggaccttcac gtggttatgt cgctgaaact tttggaactc atcttcaact tcctgatctg | 660 |
| gggccaatag cgcaaatgg tctagctgct ccaagggatt tcttgttcc tgttgcctgg | 720 |
| tacgagagatg gctcccgtcc aggttacact attgtgcaga agtatggtgg tgaactcttc | 780 |
| actgcgaagc aggacttctc tccttttaat gtggtcgctt ggcatggcaa ttatgttcct | 840 |
| tataagtatg atttaagcaa gttctgccct tacaatactg tattgatgga ccacagtgat | 900 |
| ccttcaatta acacagtttt gacagcacca acagataaac ctggtgtggc gttgcttgac | 960 |
| tttgtcattt tccctccccg gtggttggtt gctgaacaca ccttccgtcc tccatattat | 1020 |
| catcgcaatt gtatgagcga atttatgggt ctaatctatg gcggatacga ggcaaaagct | 1080 |
| gatggttttc accctggcgg ggcaagcctt cacagctgca tgactcctca tggtcctgat | 1140 |
| accaaaacat ttgaggcaac cattgcactt ggaaatgaag ctggtccaca tagaatagct | 1200 |
| gataccatgg ctttcatgtt tgagtcttgc ctagtacccc gagtctgtcc gtgggctctt | 1260 |
| gaatctccgt ttatggatca cgattattac caatgctgga ttggcttgaa gtctcacttc | 1320 |
| tcaggactat ctatgaacga agacaacgtc gatttgcaga aagggaaaac ccatagaaag | 1380 |
| ggtgaaatgc tcattgttca gctagctcct gtagttcctc ctaaagtgac ttaaagtgac | 1440 |
| ttaaacttgt acataaggag tcacaggcat gtaaaacatg aaataaaccc tatgttagta | 1500 |
| tcagattgaa agtttagggt ggcgatccaa gcgcggatat agtggtaaga tgaaaccaat | 1560 |
| gttctatgaa attgcgacgc aagtaaaaat gtgttaccgt gatgatgttg catgtaaaaa | 1620 |

<210> SEQ ID NO 27
<211> LENGTH: 477
<212> TYPE: PRT
<213> ORGANISM: Lycopersicon esculentum

<400> SEQUENCE: 27

```
His Glu Arg Thr Ser Asn Phe Pro Ser Asp Leu Glu Tyr Gln Thr Gly
 1               5                  10                  15

Phe Gly Asn His Phe Ser Ser Glu Ala Ile Val Gly Ala Leu Pro Gln
            20                  25                  30

Gly Gln Asn Ser Pro Leu Ile Cys Pro Phe Gly Leu Tyr Ala Glu Gln
        35                  40                  45

Ile Ser Gly Thr Ser Phe Thr Ser Pro Arg Lys Leu Asn Gln Arg Ser
 50                  55                  60

Trp Leu Tyr Arg Ile Lys Pro Ser Val Thr His Glu Pro Phe Arg Pro
 65                  70                  75                  80

Arg Met Pro Arg His Glu Lys Leu Val Ser Glu Phe Asn Gln Ser Asn
                85                  90                  95

Ser Ser Ala Thr Pro Thr Gln Leu Arg Trp Lys Pro Val Glu Ile Pro
            100                 105                 110

Glu Thr Pro Thr Asp Phe Ile Asp Gly Leu Tyr Thr Ile Cys Gly Ala
        115                 120                 125

Gly Ser Ser Tyr Leu Arg His Gly Phe Ala Ile His Met Tyr Thr Ala
130                 135                 140

Asn Lys Ser Met Glu Asn Ser Ala Phe Cys Asn Ala Asp Gly Asp Phe
145                 150                 155                 160

Leu Ile Val Pro Gln Lys Gly Arg Leu Trp Ile Thr Thr Glu Cys Gly
                165                 170                 175

Arg Leu Gln Val Cys Pro Gly Glu Ile Val Ile Leu Pro Gln Gly Tyr
            180                 185                 190

Arg Phe Ala Val Asp Leu Pro Asp Gly Pro Ser Arg Gly Tyr Val Ala
        195                 200                 205

Glu Thr Phe Gly Thr His Leu Gln Leu Pro Asp Leu Gly Pro Ile Gly
210                 215                 220

Ala Asn Gly Leu Ala Ala Pro Arg Asp Phe Leu Val Pro Val Ala Trp
225                 230                 235                 240

Tyr Gly Asp Gly Ser Arg Pro Gly Tyr Thr Ile Val Gln Lys Tyr Gly
                245                 250                 255

Gly Glu Leu Phe Thr Ala Lys Gln Asp Phe Ser Pro Phe Asn Val Val
            260                 265                 270

Ala Trp His Gly Asn Tyr Val Pro Tyr Lys Tyr Asp Leu Ser Lys Phe
        275                 280                 285

Cys Pro Tyr Asn Thr Val Leu Met Asp His Ser Asp Pro Ser Ile Asn
290                 295                 300

Thr Val Leu Thr Ala Pro Thr Asp Lys Pro Gly Val Ala Leu Leu Asp
305                 310                 315                 320

Phe Val Ile Phe Pro Pro Arg Trp Leu Val Ala Glu His Thr Phe Arg
                325                 330                 335

Pro Pro Tyr Tyr His Arg Asn Cys Met Ser Glu Phe Met Gly Leu Ile
            340                 345                 350

Tyr Gly Gly Tyr Glu Ala Lys Ala Asp Gly Phe His Pro Gly Gly Ala
        355                 360                 365

Ser Leu His Ser Cys Met Thr Pro His Gly Pro Asp Thr Lys Thr Phe
370                 375                 380
```

```
Glu Ala Thr Ile Ala Leu Gly Asn Glu Ala Gly Pro His Arg Ile Ala
385                 390                 395                 400
Asp Thr Met Ala Phe Met Phe Glu Ser Cys Leu Val Pro Arg Val Cys
                405                 410                 415
Pro Trp Ala Leu Glu Ser Pro Phe Met Asp His Asp Tyr Tyr Gln Cys
            420                 425                 430
Trp Ile Gly Leu Lys Ser His Phe Ser Gly Leu Ser Met Asn Glu Asp
                435                 440                 445
Asn Val Asp Leu Gln Lys Gly Lys Thr His Arg Lys Gly Glu Met Leu
    450                 455                 460
Ile Val Gln Leu Ala Pro Val Val Pro Pro Lys Val Thr
465                 470                 475

<210> SEQ ID NO 28
<211> LENGTH: 1652
<212> TYPE: DNA
<213> ORGANISM: Arabidopsis thaliana

<400> SEQUENCE: 28
```

| | | | | |
|---|---|---|---|---|
| cgatcatcgt ctctctcttt aacaagctcc tctctctgat gtgaagaagc catggaagag | 60 |
| aagaagaagg agcttgaaga gttgaagtat caatcaggtt ttggtaacca cttctcatcg | 120 |
| gaagcaatcg ccggagcttt accgttagat cagaacagtc ctcttctttg tccttacggt | 180 |
| ctttacgccg aacagatctc cggtacttct ttcacttctc ctcgcaagct caatcaaaga | 240 |
| agttggttgt accgggttaa accatcggtt acacatgaac cgttcaagcc tcgtgtacca | 300 |
| gctcataaga agcttgtgag tgagtttgat gcatcaaata gtcgtacgaa tccgactcag | 360 |
| cttcggtgga gacctgagga tattcctgat tcggagattg atttcgttga tgggttattt | 420 |
| accatttgtg gagctggaag ctcgtttctt cgccatggct cgctattca catgtatgtg | 480 |
| gctaacacag gaatgaaaga ctccgcattt tgcaacgctg atggtgactt cttgttagtt | 540 |
| cctcaaacag gaaggctatg gattgaaact gagtgtggaa ggcttttggt aactcctggt | 600 |
| gagattgctg ttataccaca aggtttccgt ttctccatag atttaccgga tgggaagtct | 660 |
| cgtggttatg ttgctgaaat ctatgggggct cattttcagc ttcctgatct tggaccaata | 720 |
| ggtgctaatg tccttgctgc atcaagagat tttcttgcac caacagcatg gtttgaggat | 780 |
| ggattgcggc ctgaatacac aattgttcag aagtttggcg tgaactctt tactgctaaa | 840 |
| caagatttct ctccattcaa tgtggttgcc tggcatggca attacgtgcc ttataagtat | 900 |
| gacctgaaga agttctgtcc atacaacact gtgcttttag atcatggaga tccatctata | 960 |
| aatacagtcc ttacagcacc aactgataaa cctggtgtgg ccttgcttga ttttgtcata | 1020 |
| tttcctcctc gatggttggt tgctgagcat acttttcgac ctccttacta tcatcgtaac | 1080 |
| tgcatgagtg aatttatggg cttaatctac ggtgcatacg aggcgaaagc tgatggattt | 1140 |
| ctccctggcg gtgcaagtct tcatagctgt atgacacctc atggtccaga tactaccacg | 1200 |
| tacgaggcga caattgctcg agtaaatgca atggctcctt ctaaactcac aggtacgatg | 1260 |
| gctttcatgt tcgaatcagc attgatcct agagtctgtc attgggctct ggagtctcct | 1320 |
| ttcctggatc acgactacta ccagtgttgg attggcctca gtctcatttt ctcgcgcata | 1380 |
| agcttggaca agacaaatgt tgaatcaaca gagaaagaac caggagcttc ggagtaaaga | 1440 |
| acacataatt cacctgcacc actttcaata cccaagctgt acagactttt caccatatac | 1500 |
| ttgtataaga aagaagcata taacaagtac atatgtaata ataagtaggt aatgtttctt | 1560 |

```
catgtcactt taaatacact atttgtactc tgaagctaat ataacggtgt tggtttagat    1620
actaatgaat ataactgtgc catttagatt ca                                  1652
```

<210> SEQ ID NO 29
<211> LENGTH: 461
<212> TYPE: PRT
<213> ORGANISM: Arabidopsis thaliana

<400> SEQUENCE: 29

```
Met Glu Glu Lys Lys Glu Leu Glu Glu Leu Lys Tyr Gln Ser Gly
1               5                   10                  15

Phe Gly Asn His Phe Ser Ser Glu Ala Ile Ala Gly Ala Leu Pro Leu
                20                  25                  30

Asp Gln Asn Ser Pro Leu Leu Cys Pro Tyr Gly Leu Tyr Ala Glu Gln
            35                  40                  45

Ile Ser Gly Thr Ser Phe Thr Ser Pro Arg Lys Leu Asn Gln Arg Ser
        50                  55                  60

Trp Leu Tyr Arg Val Lys Pro Ser Val Thr His Glu Pro Phe Lys Pro
65                  70                  75                  80

Arg Val Pro Ala His Lys Lys Leu Val Ser Glu Phe Asp Ala Ser Asn
                85                  90                  95

Ser Arg Thr Asn Pro Thr Gln Leu Arg Trp Arg Pro Glu Asp Ile Pro
            100                 105                 110

Asp Ser Glu Ile Asp Phe Val Asp Gly Leu Phe Thr Ile Cys Gly Ala
        115                 120                 125

Gly Ser Ser Phe Leu Arg His Gly Phe Ala Ile His Met Tyr Val Ala
130                 135                 140

Asn Thr Gly Met Lys Asp Ser Ala Phe Cys Asn Ala Asp Gly Asp Phe
145                 150                 155                 160

Leu Leu Val Pro Gln Thr Gly Arg Leu Trp Ile Glu Thr Glu Cys Gly
                165                 170                 175

Arg Leu Leu Val Thr Pro Gly Glu Ile Ala Val Ile Pro Gln Gly Phe
            180                 185                 190

Arg Phe Ser Ile Asp Leu Pro Asp Gly Lys Ser Arg Gly Tyr Val Ala
        195                 200                 205

Glu Ile Tyr Gly Ala His Phe Gln Leu Pro Asp Leu Gly Pro Ile Gly
    210                 215                 220

Ala Asn Gly Leu Ala Ala Ser Arg Asp Phe Leu Ala Pro Thr Ala Trp
225                 230                 235                 240

Phe Glu Asp Gly Leu Arg Pro Glu Tyr Thr Ile Val Gln Lys Phe Gly
                245                 250                 255

Gly Glu Leu Phe Thr Ala Lys Gln Asp Phe Ser Pro Phe Asn Val Val
            260                 265                 270

Ala Trp His Gly Asn Tyr Val Pro Tyr Lys Tyr Asp Leu Lys Lys Phe
        275                 280                 285

Cys Pro Tyr Asn Thr Val Leu Leu Asp His Gly Asp Pro Ser Ile Asn
    290                 295                 300

Thr Val Leu Thr Ala Pro Thr Asp Lys Pro Gly Val Ala Leu Leu Asp
305                 310                 315                 320

Phe Val Ile Phe Pro Pro Arg Trp Leu Val Ala Glu His Thr Phe Arg
                325                 330                 335

Pro Pro Tyr Tyr His Arg Asn Cys Met Ser Glu Phe Met Gly Leu Ile
            340                 345                 350

Tyr Gly Ala Tyr Glu Ala Lys Ala Asp Gly Phe Leu Pro Gly Gly Ala
```

```
                    355                 360                 365
Ser Leu His Ser Cys Met Thr Pro His Gly Pro Asp Thr Thr Thr Tyr
    370                 375                 380

Glu Ala Thr Ile Ala Arg Val Asn Ala Met Ala Pro Ser Lys Leu Thr
385                 390                 395                 400

Gly Thr Met Ala Phe Met Phe Glu Ser Ala Leu Ile Pro Arg Val Cys
                405                 410                 415

His Trp Ala Leu Glu Ser Pro Phe Leu Asp His Asp Tyr Tyr Gln Cys
            420                 425                 430

Trp Ile Gly Leu Lys Ser His Phe Ser Arg Ile Ser Leu Asp Lys Thr
        435                 440                 445

Asn Val Glu Ser Thr Glu Lys Glu Pro Gly Ala Ser Glu
    450                 455                 460
```